（12) United States Patent
Dougherty et al.

(10) Patent No.: US 10,575,994 B2
(45) Date of Patent: *Mar. 3, 2020

(54) TAMPON ASSEMBLY PROVIDING PROPER BODILY PLACEMENT OF PLEDGET

(71) Applicant: Edgewell Personal Care Brands, LLC, Chesterfield, MO (US)

(72) Inventors: Eugene P Dougherty, Newark, DE (US); Phillip Ebert, Camden/Wyoming, DE (US); Keith Edgett, Middletown, DE (US)

(73) Assignee: Edgewell Personal Care Brands, LLC, Chesterfield, MO (US)

( * ) Notice: Subject to any disclaimer, the term of this patent is extended or adjusted under 35 U.S.C. 154(b) by 180 days.

This patent is subject to a terminal disclaimer.

(21) Appl. No.: 15/452,180

(22) Filed: Mar. 7, 2017

(65) Prior Publication Data

US 2017/0172812 A1   Jun. 22, 2017

Related U.S. Application Data

(63) Continuation of application No. 14/189,279, filed on Feb. 25, 2014, now Pat. No. 9,820,890, which is a
(Continued)

(51) Int. Cl.
*A61F 13/20* (2006.01)
*A61F 13/26* (2006.01)
(Continued)

(52) U.S. Cl.
CPC .......... *A61F 13/266* (2013.01); *A61F 13/202* (2013.01); *A61F 13/204* (2013.01);
(Continued)

(58) Field of Classification Search
CPC ................ A61F 13/204; A61F 13/2051; A61F 13/2054; A61F 13/208; A61F 13/26; A61F 13/266; A61F 13/28; A61F 13/34
See application file for complete search history.

(56) References Cited

U.S. PATENT DOCUMENTS 1,191,736 A   7/1916   Roberson
1,218,478 A   3/1917   Sappington
(Continued)

FOREIGN PATENT DOCUMENTS

AU   8774659   1/1988
BE   667613    1/1966
(Continued)

OTHER PUBLICATIONS

Final Office Action of U.S. Appl. No. 11/811,705, dated Mar. 17, 2010.
(Continued)

*Primary Examiner* — Catharine L Anderson

(57) ABSTRACT

Provided is a tampon applicator having one or more insertion indicators to gauge and/or control the insertion depth of a tampon. The one or more insertion indicators may be located on the tampon applicator barrel, plunger, tampon, removal string, or any combinations thereof. As a result of the one or more insertion indicators, a woman can adjust the insertion depth of the tampon to her body's requirements ensuring leakage protection, comfort, or both.

7 Claims, 21 Drawing Sheets

Related U.S. Application Data continuation of application No. 12/886,049, filed on Sep. 20, 2010, now abandoned, which is a continuation of application No. 11/811,705, filed on Jun. 12, 2007, now Pat. No. 7,815,594.

(60) Provisional application No. 60/812,759, filed on Jun. 12, 2006.

(51) Int. Cl.
   A61F 13/32    (2006.01)
   A61F 13/28    (2006.01)
   A61F 13/34    (2006.01)
   A61F 13/84    (2006.01)

(52) U.S. Cl.
   CPC .......... *A61F 13/2068* (2013.01); *A61F 13/26* (2013.01); *A61F 13/263* (2013.01); *A61F 13/28* (2013.01); *A61F 13/34* (2013.01); *A61F 13/84* (2013.01); *A61F 2013/8497* (2013.01)

(56) References Cited

U.S. PATENT DOCUMENTS

| | | |
|---|---|---|
| 1,554,690 A | 9/1925 | Pride |
| 1,555,708 A | 9/1925 | Gale |
| 1,731,665 A | 10/1929 | Huebsch |
| 2,077,231 A | 4/1937 | Fourness et al. |
| 2,095,377 A | 10/1937 | Breese |
| 2,099,931 A | 11/1937 | Fourness |
| 2,123,750 A | 7/1938 | Schulz |
| 2,178,704 A | 11/1939 | Robinson |
| 2,222,088 A | 11/1940 | Petersen |
| 2,254,272 A | 9/1941 | Crockford |
| 2,301,868 A | 11/1942 | Gurley et al. |
| 2,306,406 A | 12/1942 | Robinson |
| 2,330,257 A | 9/1943 | Bailey |
| 2,386,590 A | 10/1945 | Calhoun |
| 2,413,480 A | 12/1946 | Winter |
| 2,458,685 A | 1/1949 | Crockford |
| 2,476,956 A | 7/1949 | Bonham |
| 2,489,502 A | 11/1949 | Ruth |
| 2,409,414 A | 3/1950 | Rabell |
| 2,499,444 A | 3/1950 | Alison |
| 2,607,346 A | 8/1952 | Milcent |
| 2,706,986 A | 4/1955 | Carrier |
| 2,761,449 A | 9/1956 | Bletzinger |
| 2,799,055 A | 7/1957 | Carrier |
| 2,654,978 A | 10/1958 | Millman et al. |
| 2,877,767 A | 3/1959 | Schwartz |
| 3,042,040 A | 7/1962 | Galik |
| 3,204,635 A | 9/1965 | Voss et al. |
| 3,264,691 A | 8/1966 | Whitehead |
| 3,291,130 A | 12/1966 | Whitehead |
| 3,306,294 A | 2/1967 | Penska |
| 3,306,295 A | 2/1967 | Penska |
| 3,347,234 A | 10/1967 | Voss |
| 3,358,354 A | 12/1967 | Voss et al. |
| 3,369,544 A | 2/1968 | Crockford |
| 3,397,695 A | 8/1968 | Voss |
| 3,431,909 A | 3/1969 | Krusko |
| 3,431,910 A | 3/1969 | Kokx |
| 3,433,225 A | 3/1969 | Voss et al. |
| 3,520,302 A | 7/1970 | Jones |
| 3,570,489 A | 3/1971 | Brown |
| 3,572,341 A * | 3/1971 | Glassman ........... A61F 13/2068 604/359 |
| 3,575,169 A | 4/1971 | Voss et al. |
| 3,595,236 A | 7/1971 | Corrigan |
| 3,628,533 A | 12/1971 | Loyer |
| 3,643,661 A | 2/1972 | Crockford |
| 3,683,915 A | 8/1972 | Voss |
| 3,690,321 A | 9/1972 | Hirschman |
| 3,695,270 A | 10/1972 | Dosta |
| 3,706,311 A | 12/1972 | Kokx et al. |
| 3,710,793 A | 1/1973 | Glassman |
| 3,712,305 A | 1/1973 | Wennerblom et al. |
| 3,726,277 A | 4/1973 | Hirschman |
| 3,731,687 A | 5/1973 | Glassman |
| 3,738,364 A | 6/1973 | Brien et al. |
| 3,762,413 A | 10/1973 | Hanke |
| 3,765,416 A | 10/1973 | Werner et al. |
| 3,794,029 A | 2/1974 | Dulle |
| 3,812,856 A | 5/1974 | Duncan et al. |
| 3,834,389 A | 9/1974 | Dulle |
| 3,845,767 A | 11/1974 | Friese et al. |
| 3,856,013 A | 12/1974 | Dulle |
| 3,858,571 A | 1/1975 | Rudolph |
| 3,885,563 A | 5/1975 | Johnson et al. |
| 3,905,372 A | 9/1975 | Denkinger |
| 3,946,737 A | 3/1976 | Kohler |
| 3,954,104 A | 5/1976 | Kraskin et al. |
| 3,971,378 A | 7/1976 | Krantz |
| 3,981,305 A | 9/1976 | Ring |
| 3,983,783 A | 10/1976 | Hirschman |
| 3,994,298 A | 11/1976 | Des Marais |
| 4,010,751 A | 3/1977 | Ring |
| 4,018,255 A | 4/1977 | Diggs |
| 4,027,673 A | 6/1977 | Poncy et al. |
| 4,048,998 A | 9/1977 | Nigro |
| 4,077,408 A | 3/1978 | Murray et al. |
| 4,077,409 A | 3/1978 | Murray et al. |
| 4,099,976 A | 7/1978 | Kraskin et al. |
| 4,108,180 A | 8/1978 | Moehrle |
| D250,663 S | 12/1978 | Koch et al. |
| 4,175,457 A | 11/1979 | Lashey |
| 4,185,631 A | 1/1980 | McConnell |
| 4,186,742 A | 2/1980 | Donald |
| 4,198,978 A | 4/1980 | Nigro |
| 4,211,225 A | 7/1980 | Sibalis |
| 4,212,301 A | 7/1980 | Johnson |
| 4,217,900 A | 8/1980 | Wegner et al. |
| 4,266,546 A | 5/1981 | Roland et al. |
| 4,271,835 A | 6/1981 | Conn et al. |
| 4,274,412 A | 6/1981 | Austin |
| 4,278,088 A | 7/1981 | Reeves et al. |
| 4,291,696 A | 9/1981 | Ring |
| 4,294,253 A | 10/1981 | Friese |
| 4,308,867 A | 1/1982 | Roseman et al. |
| 4,309,997 A | 1/1982 | Donald |
| 4,312,348 A | 1/1982 | Friese |
| 4,318,407 A | 3/1982 | Woon |
| 4,328,804 A | 5/1982 | Shimatani |
| 4,335,720 A | 6/1982 | Gassman |
| 4,335,721 A | 6/1982 | Matthews |
| 4,341,211 A | 7/1982 | Kline |
| 4,341,214 A | 7/1982 | Fries et al. |
| 4,351,339 A | 9/1982 | Sneider |
| 4,361,150 A | 11/1982 | Voss |
| 4,361,151 A | 11/1982 | Fitzgerald |
| 4,373,529 A | 2/1983 | Lilaonitkul et al. |
| 4,421,504 A | 12/1983 | Kine |
| 4,424,054 A | 1/1984 | Conn et al. |
| 4,424,370 A | 1/1984 | Keely |
| 4,475,911 A | 10/1984 | Gellert |
| D279,504 S | 7/1985 | Tump |
| 4,536,178 A | 8/1985 | Lichstein et al. |
| 4,543,086 A | 9/1985 | Johnson |
| 4,543,098 A | 9/1985 | Wolfe et al. |
| 4,553,965 A | 11/1985 | Conn et al. |
| D287,876 S | 1/1987 | Blatherwick et al. |
| 4,676,773 A | 6/1987 | Sheldon |
| 4,726,805 A | 2/1988 | Sanders, III |
| 4,743,237 A | 5/1988 | Olmstead |
| 4,755,166 A | 7/1988 | Sweere |
| 4,787,895 A | 11/1988 | Stokes et al. |
| 4,822,332 A | 4/1989 | Kaander |
| 4,845,922 A | 7/1989 | Sanders, III |
| 4,846,802 A | 7/1989 | Melvin et al. |
| 4,891,042 A | 1/1990 | Hoden et al. |
| 5,019,061 A | 5/1991 | Glassman |
| 5,047,024 A | 9/1991 | Sheldon et al. |
| 5,084,038 A | 1/1992 | Sheldon et al. |
| 5,112,348 A | 5/1992 | Glassman |

(56) References Cited

U.S. PATENT DOCUMENTS

| | | | |
|---|---|---|---|
| 5,149,332 A | 9/1992 | Walton et al. | |
| 5,153,971 A | 10/1992 | Van Iten | |
| 5,158,535 A | 10/1992 | Paul et al. | |
| 5,213,566 A | 5/1993 | Weissenburger | |
| 5,267,953 A | 12/1993 | Paul et al. | |
| 5,278,541 A | 1/1994 | Frayman et al. | |
| 5,342,331 A | 8/1994 | Silber et al. | |
| 5,350,371 A | 9/1994 | Van Iten | |
| 5,364,383 A | 11/1994 | Hayes et al. | |
| 5,370,663 A | 12/1994 | Villalta | |
| 5,387,206 A | 2/1995 | Valentine et al. | |
| 5,395,308 A | 3/1995 | Fox et al. | |
| 5,403,300 A | 4/1995 | Howarth | |
| 5,417,224 A | 5/1995 | Petrus et al. | |
| 5,437,628 A | 8/1995 | Fox et al. | |
| 5,443,776 A | 8/1995 | Bartholomew et al. | |
| 5,445,605 A | 8/1995 | Pluss | |
| 5,542,914 A | 8/1996 | Van Iten | |
| 5,547,701 A | 8/1996 | Nielsen et al. | |
| 5,554,108 A | 9/1996 | Browning et al. | |
| 5,584,827 A | 12/1996 | Korteweg et al. | |
| 5,592,725 A | 1/1997 | Brinker | |
| 5,634,248 A | 6/1997 | McNelis et al. | |
| 5,638,646 A | 6/1997 | Shane | |
| 5,659,934 A | 8/1997 | Jessup et al. | |
| 5,662,601 A | 9/1997 | Snead | |
| 5,681,894 A | 10/1997 | Williams et al. | |
| 5,683,358 A | 11/1997 | Nielsen et al. | |
| 5,693,009 A | 12/1997 | Fax et al. | |
| 5,709,652 A | 1/1998 | Hagerty | |
| 5,718,675 A | 2/1998 | Leljd | |
| 5,755,906 A | 5/1998 | Achter et al. | |
| 5,766,145 A | 6/1998 | Fox et al. | |
| 5,772,645 A | 6/1998 | Zadin et al. | |
| 5,788,663 A | 8/1998 | Igaue et al. | |
| 5,792,096 A | 8/1998 | Rentmeester et al. | |
| 5,795,346 A | 8/1998 | Achter et al. | |
| 5,800,338 A | 9/1998 | Kollerup et al. | |
| 5,807,372 A | 9/1998 | Balzar | |
| 5,817,047 A | 10/1998 | Osborn, III et al. | |
| 5,827,251 A | 10/1998 | Moder et al. | |
| 5,873,971 A | 2/1999 | Balzar | |
| 5,891,123 A | 4/1999 | Bazar | |
| 5,891,127 A | 4/1999 | Moder et al. | |
| 5,911,712 A | 6/1999 | Leutwyler et al. | |
| 5,928,183 A | 7/1999 | Fox et al. | |
| 5,928,184 A | 7/1999 | Etheredge et al. | |
| 5,947,992 A | 9/1999 | Zadini et al. | |
| 5,964,741 A | 10/1999 | Moder et al. | |
| 5,986,000 A | 11/1999 | Williams et al. | |
| 5,986,165 A | 11/1999 | Moder et al. | |
| 5,988,386 A | 11/1999 | Morrow | |
| 6,003,216 A | 12/1999 | Hull, Jr. et al. | |
| 6,019,743 A | 2/2000 | Cole et al. | |
| 6,039,716 A | 3/2000 | Jessup et al. | |
| 6,039,828 A | 3/2000 | Achter et al. | |
| 6,068,899 A | 5/2000 | Osborn, III et al. | |
| 6,071,259 A | 6/2000 | Steiger et al. | |
| 6,090,038 A | 7/2000 | Zenker et al. | |
| 6,095,998 A | 8/2000 | Osborn et al. | |
| 6,142,928 A | 11/2000 | Zenker et al. | |
| 6,168,576 B1 | 1/2001 | Reynolds | |
| 6,177,606 B1 | 1/2001 | Etheredge et al. | |
| 6,177,608 B1 | 1/2001 | Weinstrauch | |
| 6,180,051 B1 | 1/2001 | Schoelling | |
| 6,183,436 B1 | 2/2001 | Korteweg et al. | |
| 6,186,994 B1 | 2/2001 | Bowles et al. | |
| 6,186,995 B1 | 2/2001 | Tharpe, Jr. | |
| 6,190,348 B1 | 2/2001 | Tiemann et al. | |
| 6,191,341 B1 | 2/2001 | Shippert | |
| 6,196,988 B1 | 3/2001 | Cole et al. | |
| 6,206,867 B1 | 3/2001 | Osborn, III et al. | |
| 6,254,565 B1 | 7/2001 | Williams et al. | |
| 6,254,566 B1 | 7/2001 | Buck et al. | |
| 6,258,075 B1 | 7/2001 | Taylor et al. | |
| 6,264,626 B1 | 7/2001 | Linares et al. | |
| 6,270,470 B1 | 8/2001 | Buck et al. | |
| 6,283,952 B1 | 9/2001 | Child et al. | |
| 6,299,573 B1 | 10/2001 | Hull, Jr. et al. | |
| 6,302,861 B2 | 10/2001 | Tweddell, III et al. | |
| 6,302,862 B1 | 10/2001 | Osborn, III et al. | |
| 6,310,269 B1 | 10/2001 | Friese | |
| 6,358,235 B1 | 3/2002 | Osborn, III et al. | |
| 6,368,442 B1 | 4/2002 | Linares et al. | |
| 6,380,455 B1 | 4/2002 | Moder et al. | |
| 6,416,488 B1 | 7/2002 | Jackson et al. | |
| 6,419,777 B1 | 7/2002 | Achter et al. | |
| 6,423,025 B1 | 7/2002 | Buzot | |
| 6,432,075 B1 | 8/2002 | Wada et al. | |
| 6,432,076 B1 * | 8/2002 | Wada | A61F 13/26 604/15 |
| 6,432,246 B1 | 8/2002 | Blake | |
| 6,450,986 B1 | 9/2002 | Binner et al. | |
| 6,465,713 B1 | 10/2002 | Gell et al. | |
| 6,478,726 B1 | 11/2002 | Zunker | |
| 6,478,764 B1 | 11/2002 | Suga | |
| D467,599 S | 12/2002 | Brazell | |
| 6,500,140 B1 | 12/2002 | Cole et al. | |
| 6,508,780 B1 | 1/2003 | Edgett et al. | |
| 6,511,452 B1 | 1/2003 | Rejai et al. | |
| 6,570,052 B2 | 5/2003 | Zadini et al. | |
| 6,572,577 B1 | 6/2003 | Binner et al. | |
| D477,075 S | 7/2003 | Schoelling | |
| 6,585,300 B1 | 7/2003 | Rajala et al. | |
| 6,603,054 B2 | 8/2003 | Chen et al. | |
| 6,610,025 B2 | 8/2003 | Berg et al. | |
| 6,645,136 B1 | 11/2003 | Zunker et al. | |
| 6,648,846 B2 | 11/2003 | Binner et al. | |
| 6,654,992 B2 | 12/2003 | Rajala et al. | |
| 6,679,868 B2 | 1/2004 | Kostadimas | |
| 6,685,767 B2 | 2/2004 | Linares et al. | |
| 6,685,788 B2 | 2/2004 | Linares et al. | |
| 6,730,057 B2 | 5/2004 | Zhao et al. | |
| 6,740,070 B2 | 5/2004 | Agyapong et al. | |
| 6,756,434 B1 | 6/2004 | Williams et al. | |
| 6,773,423 B2 | 8/2004 | Osborn et al. | |
| 6,830,554 B2 | 12/2004 | Jackson et al. | |
| 6,887,226 B2 | 5/2005 | Casoni et al. | |
| 6,932,805 B2 | 8/2005 | Domeier et al. | |
| 6,958,057 B2 | 10/2005 | Berg et al. | |
| 7,044,928 B2 | 5/2006 | LeMay et al. | |
| 7,081,110 B2 | 7/2006 | Karapasha | |
| 7,098,292 B2 | 8/2006 | Zhao et al. | |
| 7,172,573 B2 | 2/2007 | Lamb et al. | |
| 7,241,274 B2 | 7/2007 | Suga | |
| 7,259,129 B2 | 7/2007 | Williams et al. | |
| 7,335,194 B2 | 2/2008 | Wada | |
| D639,864 S | 6/2011 | Woelfel | |
| D652,848 S | 1/2012 | Flanagan et al. | |
| 9,107,775 B2 | 8/2015 | Edgett et al. | |
| 9,820,890 B2 * | 11/2017 | Dougherty | A61F 13/26 |
| 2002/0010413 A1 | 1/2002 | Binner et al. | |
| 2002/0107497 A1 | 8/2002 | Osborn, III et al. | |
| 2002/0133135 A1 | 9/2002 | Gell et al. | |
| 2002/0143287 A1 | 10/2002 | Buzot | |
| 2002/0143303 A1 | 10/2002 | Intravartolo et al. | |
| 2002/0147436 A1 | 10/2002 | Gell et al. | |
| 2002/0151859 A1 | 10/2002 | Schoelling | |
| 2002/0177835 A1 | 11/2002 | Zadini et al. | |
| 2002/0183681 A1 | 12/2002 | Bernard | |
| 2002/0188283 A1 | 12/2002 | Binner et al. | |
| 2003/0028176 A1 | 2/2003 | Berg et al. | |
| 2003/0028177 A1 | 2/2003 | Berg et al. | |
| 2003/0040695 A1 | 2/2003 | Zhao et al. | |
| 2003/0055391 A1 | 3/2003 | Nguyen et al. | |
| 2003/0073948 A1 | 4/2003 | Binner et al. | |
| 2003/0105421 A1 | 6/2003 | Jarmon et al. | |
| 2003/0125658 A1 | 7/2003 | Marvin | |
| 2003/0135180 A1 | 7/2003 | Marvin | |
| 2003/0149416 A1 | 8/2003 | Cole et al. | |
| 2003/0158533 A1 | 8/2003 | Agyapong et al. | |
| 2003/0167048 A1 | 9/2003 | Policappelli | |
| 2003/0172504 A1 | 9/2003 | Sageser et al. | |
| 2003/0176844 A1 | 9/2003 | Policappelli | |

(56) References Cited

U.S. PATENT DOCUMENTS

| | | | |
|---|---|---|---|
| 2003/0176845 | A1 | 9/2003 | Sagesar et al. |
| 2003/0208179 | A1 | 11/2003 | Fuchs et al. |
| 2003/0208180 | A1 | 11/2003 | Fuchs et al. |
| 2003/0216680 | A1 | 11/2003 | Fuchs et al. |
| 2003/0236485 | A1 | 12/2003 | Fedyk et al. |
| 2004/0054317 | A1 | 3/2004 | Lemay et al. |
| 2004/0064082 | A1 | 3/2004 | LeMay et al. |
| 2004/0193131 | A1 | 9/2004 | Wada |
| 2004/0199101 | A1 | 10/2004 | LeMay et al. |
| 2004/0199102 | A1 | 10/2004 | LeMay et al. |
| 2004/0243088 | A1 | 12/2004 | LeMay et al. |
| 2005/0015041 | A1 | 1/2005 | Karapasha |
| 2005/0070645 | A1 | 3/2005 | Williams et al. |
| 2005/0080393 | A1 | 4/2005 | Policappelli |
| 2005/0096619 | A1 | 5/2005 | Costa |
| 2005/0171463 | A1* | 8/2005 | Suga ............... A61F 13/26 604/15 |
| 2005/0177091 | A1 | 8/2005 | Jarmon et al. |
| 2006/0004319 | A1 | 1/2006 | Berg, Jr. et al. |
| 2006/0004320 | A1 | 1/2006 | Berg, Jr. et al. |
| 2006/0221502 | A1 | 10/2006 | Watanabe et al. |
| 2007/0026228 | A1 | 2/2007 | Hartmann et al. |
| 2007/0156081 | A1 | 7/2007 | Karapasha |
| 2007/0232982 | A1 | 10/2007 | Jarmon et al. |
| 2007/0260211 | A1 | 11/2007 | Schmidt-Forst |
| 2007/0276317 | A1 | 11/2007 | Henderson et al. |
| 2007/0293809 | A1 | 12/2007 | Karapasha |
| 2009/0156979 | A1 | 6/2009 | Andersch |

FOREIGN PATENT DOCUMENTS

| | | |
|---|---|---|
| BE | 758152 | 4/1971 |
| CA | 11086099 | 9/1980 |
| CA | 1110401 | 10/1981 |
| CA | 2024473 | 3/1991 |
| CA | 2095390 | 11/1993 |
| CA | 2143083 | 2/1996 |
| CA | 2145692 | 2/1996 |
| CA | 2153818 | 2/1996 |
| CA | 2280251 | 2/2000 |
| CA | 2302065 | 9/2000 |
| CA | 2325269 | 5/2001 |
| CA | 2325669 | 5/2001 |
| DE | 1920773 | 12/1969 |
| DE | 3326910 | 2/1985 |
| DE | 3540725 | 5/1986 |
| DE | 3609852 | 9/1987 |
| DE | 3726311 | 2/1989 |
| DE | 4446226 | 6/1995 |
| DE | 19726648 | 12/1998 |
| DE | 19747633 | 3/1999 |
| EP | 110793 | 12/1983 |
| EP | 158543 | 3/1985 |
| EP | 0243250 | 10/1987 |
| EP | 546256 | 7/1992 |
| EP | 797971 | 10/1997 |
| FR | 1515087 | 3/1968 |
| FR | 2207687 | 6/1974 |
| FR | 2567399 | 7/1984 |
| GB | 2073592 | 10/1981 |
| GB | 2097259 | 11/1982 |
| GB | 8428462 | 12/1984 |
| GB | 9419135 | 11/1994 |
| IL | 154877 | 7/2009 |
| IL | 163734 | 12/2009 |
| JP | 62-8754 | 1/1987 |
| JP | 63-212358 | 9/1988 |
| JP | H05-68695 | 3/1993 |
| JP | 10024064 | 1/1998 |
| JP | 2000288018 | 10/2000 |
| JP | 2001-008964 | 1/2001 |
| JP | 200117465 | 1/2001 |
| JP | 2001145658 | 5/2001 |
| JP | 2005-526584 | 9/2005 |
| JP | SHO62-027952 | 9/2005 |
| JP | 2005531345 | 10/2005 |
| WO | WO8000008 | 1/1980 |
| WO | WO93/08779 | 5/1993 |
| WO | 94/15564 | 7/1994 |
| WO | 9605795 | 2/1996 |
| WO | 9637173 | 11/1996 |
| WO | 9640032 | 12/1996 |
| WO | 9806366 | 2/1998 |
| WO | 9900097 | 1/1999 |
| WO | 0037013 | 6/2000 |
| WO | 0066213 | 11/2000 |
| WO | 02074352 | 9/2001 |
| WO | 0197735 | 12/2001 |
| WO | 0200153 | 1/2002 |
| WO | 0202176 | 1/2002 |
| WO | 0226159 | 4/2002 |
| WO | 03032883 | 4/2003 |
| WO | WO2003101362 | 11/2003 |
| WO | 200400160 | 12/2003 |
| WO | 2005112856 A1 | 12/2005 |
| WO | 2005112862 A1 | 12/2005 |
| WO | 2006016933 A1 | 2/2006 |
| WO | 2006037157 | 4/2006 |
| WO | 2004/098449 | 11/2006 |
| WO | 2007078413 A1 | 7/2007 |
| ZA | 9305011 | 2/1994 |

OTHER PUBLICATIONS

Advisory Action of U.S. Appl. No. 11/811,705, dated Feb. 25, 2009.
Final Office Action of U.S. Appl. No. 11/811,705, dated Dec. 2, 2008.
Final Office Action of U.S. Appl. No. 12/866,049, dated Oct. 21, 2013.
Non-Final Office Action of U.S. Appl. No. 12/866,049, dated Apr. 22, 2013.
Restriction Requirement of U.S. Appl. No. 12/866,049, dated Mar. 13, 2013.
Non-Final Office Action of U.S. Appl. No. 14/189,279, dated Jun. 24, 2015.
Final Office Action of U.S. Appl. No. 14/189,279, dated Dec. 11, 2015.
Advisory Action of U.S. Appl. No. 14/189,279, dated Mar. 22, 2016.
Non-Final Office Action of U.S. Appl. No. 14/189,279, dated Jun. 7, 2016.
Final Office Action of U.S. Appl. No. 14/189,279, dated Oct. 13, 2016.

* cited by examiner

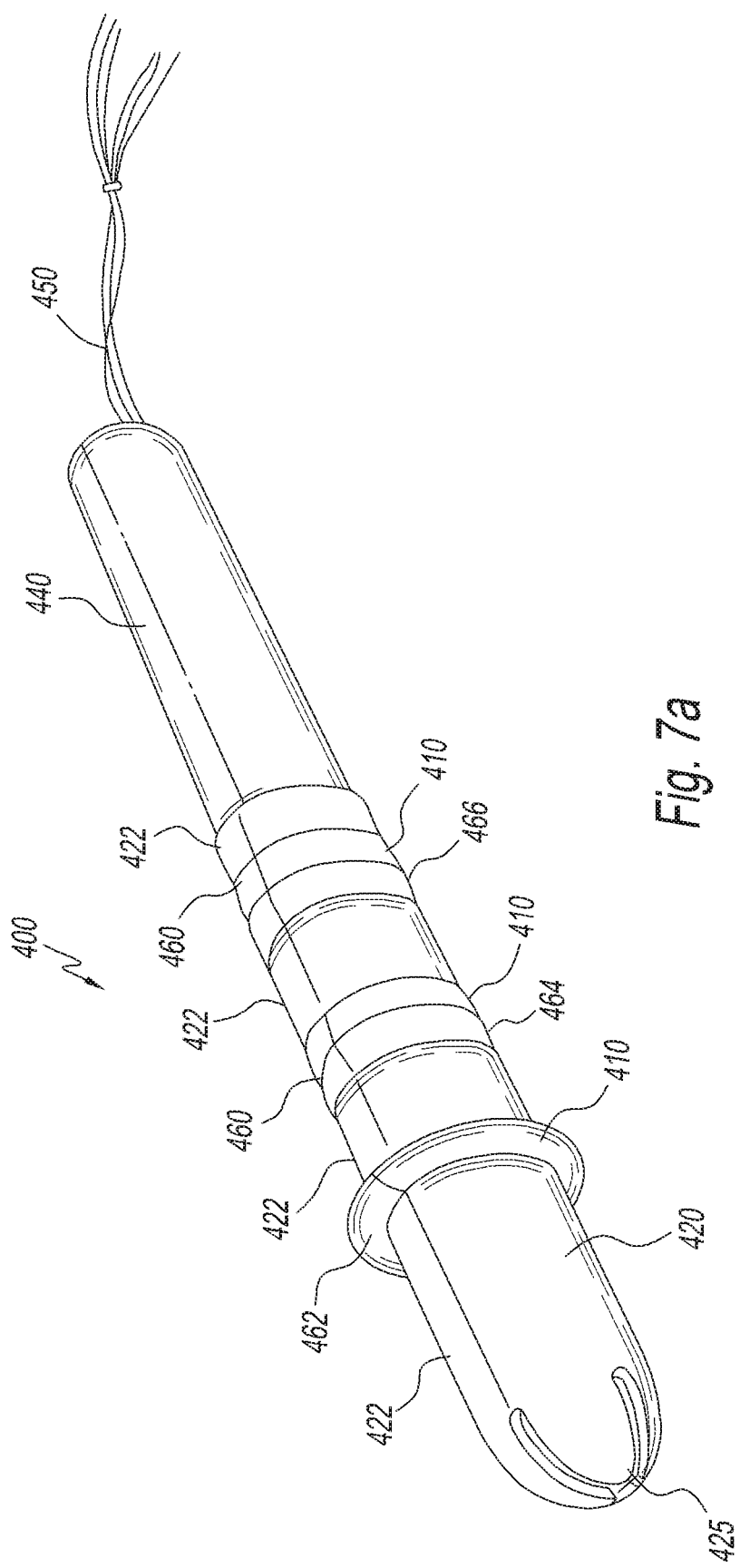

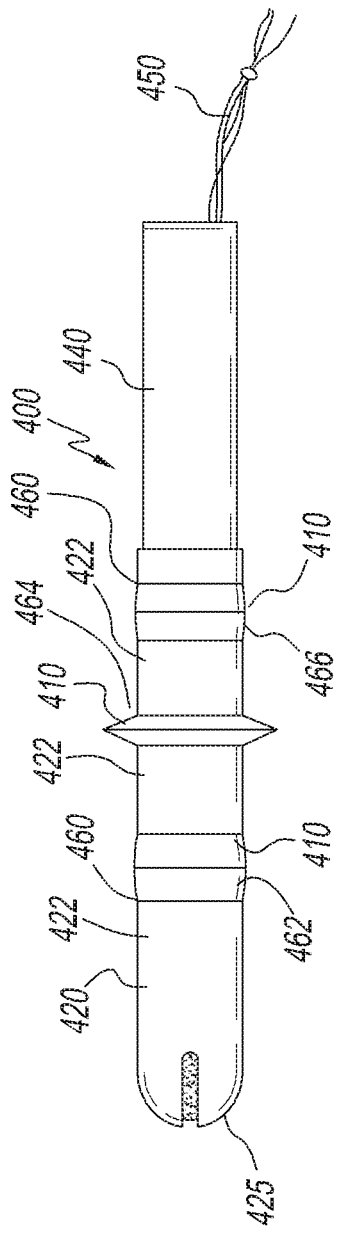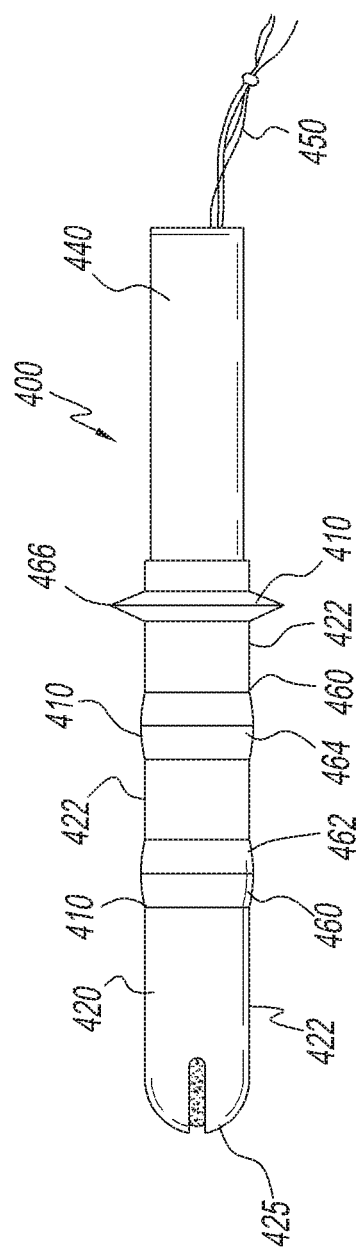
Fig. 7b
Fig. 7c

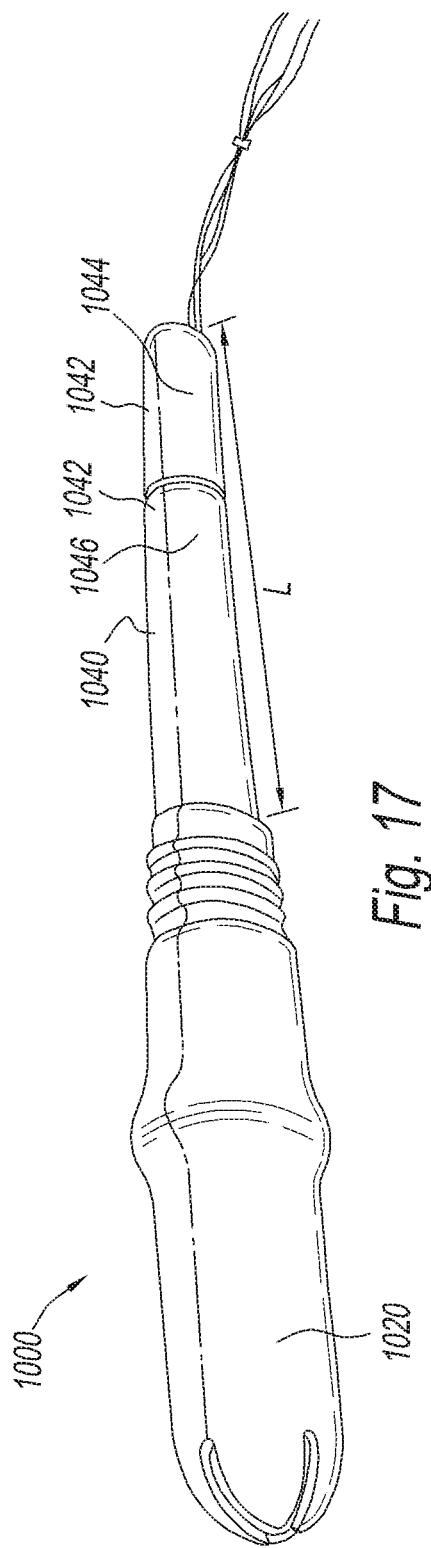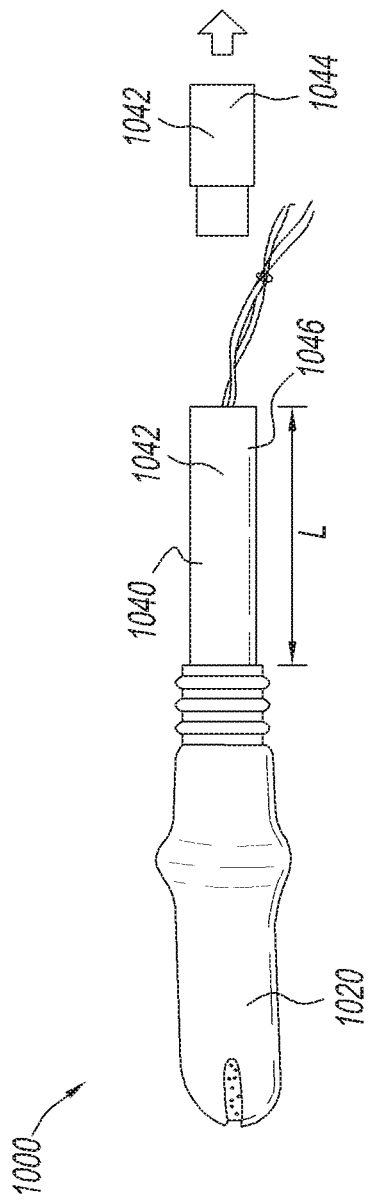

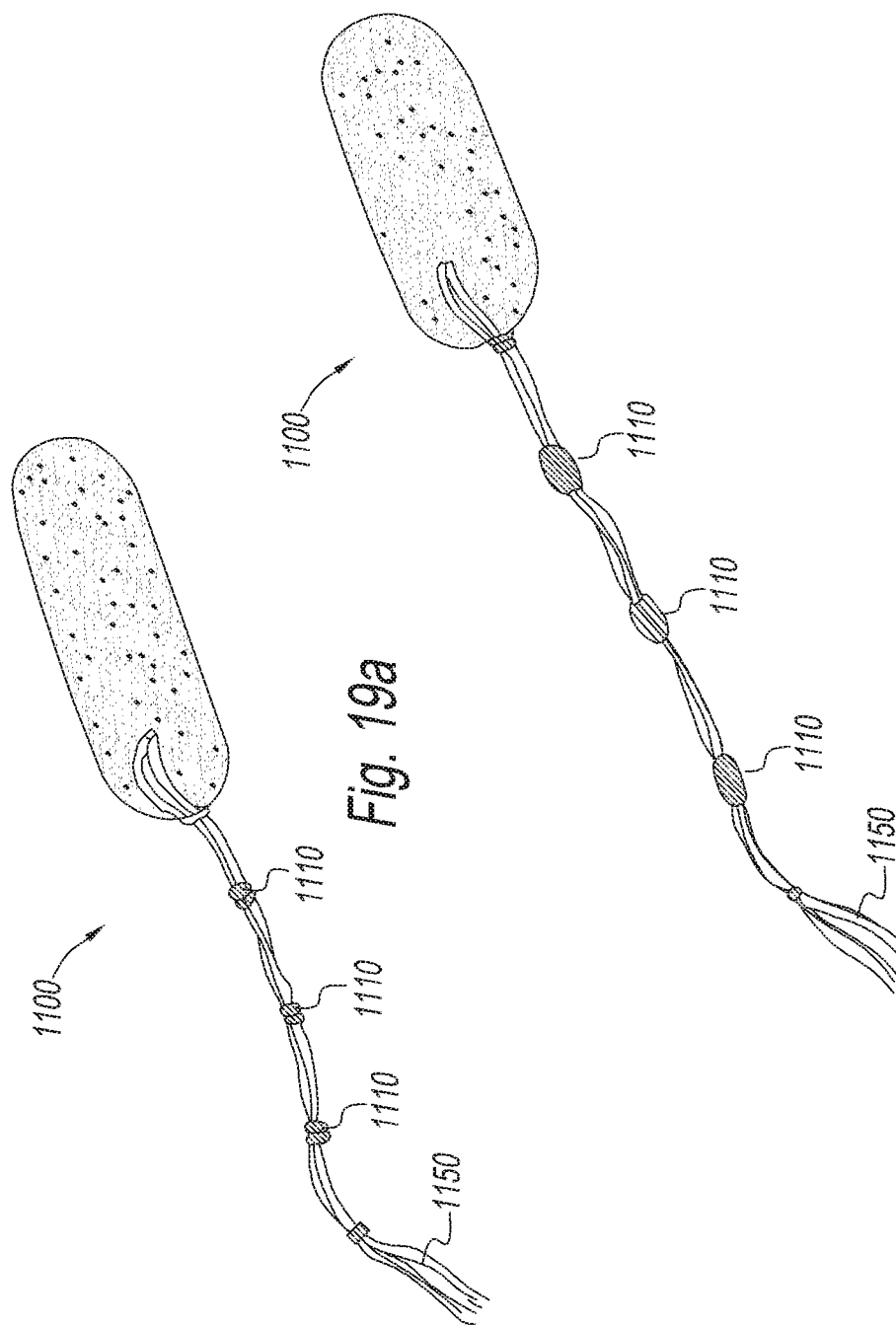

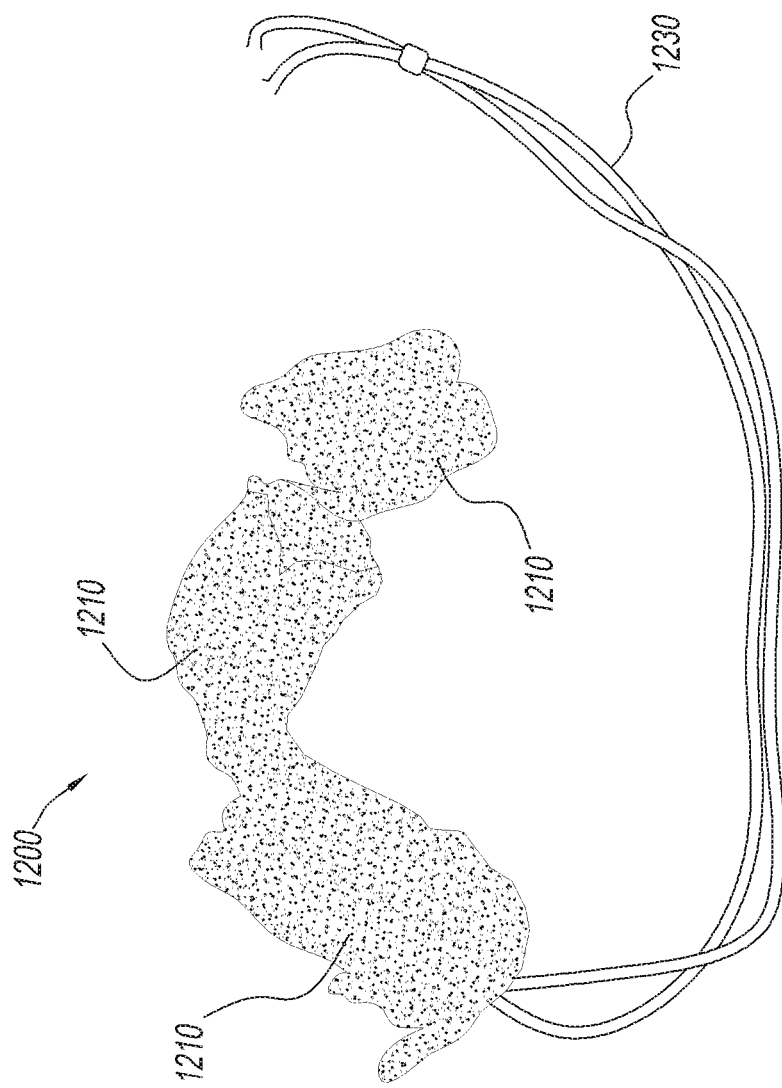

TAMPON ASSEMBLY PROVIDING PROPER BODILY PLACEMENT OF PLEDGET

CROSS-REFERENCE TO RELATED APPLICATION

This application is a continuation application of U.S. patent application Ser. No. 14/189,279, filed on Feb. 25, 2014, which is a divisional application of prior U.S. patent application Ser. No. 12/886,049, filed Sep. 20, 2010, now abandoned, which is a continuation of prior application Ser. No. 11/811,705, filed Jun. 12, 2007, which claims the benefit of U.S. Provisional Application No. 60/812,759, filed Jun. 12, 2006. The contents of application Ser. No. 11/811,705, filed Jun. 12, 2007, and U.S. Provisional Application No. 60/812,759, filed Jun. 12, 2006, are each hereby incorporated by reference in their entirety.

FIELD OF THE INVENTION

The present invention relates generally to a tampon assembly. The present invention more particularly relates to a tampon assembly that provides proper bodily placement of a tampon pledget.

BACKGROUND OF THE INVENTION

It is well known that the pelvic regions in women's bodies can exhibit wide variation. Some women have large bladders and short vaginas, while others have long or wide-set vaginal canals with tiny bladders. Some women are large, others quite petite. Vaginal canals can be conical in shape, cylindrical, rectangular, or "slug-shaped". Some women have ovarian cysts, fibroids, or congenital defects, such as, uterine septa. Over time, women's bodies also change. For instance, over a course of hours, bladders fill up and then empty. Over the course of many years, vaginal muscles weaken, and vaginal and uterine prolapse can occur.

During menstruation, all these anatomical differences can be quite important. In the prior art, tampon design has typically focused on improving and controlling absorbency on the one hand and insertion/removal comfort on the other. But these are not the only factors in designing a tampon. Designing a tampon to ensure both protection against leakage of menstrual fluid as well as wearer comfort to accommodate such large anatomical variations as exhibited in women, is a challenge that feminine care technology has not yet quite met. With today's current tampon offerings, women's choices are limited and, in some instances, inadequate to achieve these goals.

To illustrate the various anatomical variations and resulting tampon pledget placement variations, an MRI study was conducted. MRI images are provided in FIGS. 1 and 2 for two different women. The woman whose MRI image appears in FIG. 1 had a tampon pledget 10 inserted up much higher, above her bladder 12, and did complain of leakage. The woman whose MRI image appears in FIG. 2 had a tampon pledget 14 inserted low, below a midpoint of her bladder 16, with significant absorption of menses. These MRI's suggest that if a tampon pledget is positioned too far up a user's vaginal cavity, there is possible bypass leakage, and if the tampon pledget is placed too low in the vaginal cavity, the user may experience discomfort or the pledget may even fall out.

Referring to FIG. 3, another MRI view of a tampon pledget in a woman's body is shown. As this coronal scan shows, the pledget 18 is almost horizontal and oriented almost at a right angle to the source of menstrual bleeding, the cervical os 20. Clearly, pledget 18 is placed up too high in the user's vaginal fornix. The pledget is not oriented below the cervical os 20, and as a result leakage is likely to occur, mainly because of gravity.

To complement the MRI data, inspection of used tampon pledgets suggests that absorption often occurs only on one side of the pledget, including when a woman complains of leakage. It is likely that the pledget was not properly placed inside the vagina, since most of the discoloration is on one side. If the pledget were better positioned with respect to the cervical os, absorption would be more uniform throughout the pledget, and leakage may likely be prevented.

In view of the above, tampon pledget placement is clearly affected by a variety of factors, including, but not limited to, a woman's habits and practices, age, anatomical differences, weight, pressure of surrounding tissues, especially the bladder, colon and/or pelvic floor, or any combination of factors thereof. Therefore, there remains a need in the art for a tampon assembly that provides proper bodily placement of a tampon pledget.

The present invention meets this need and provides a variety of means to ensure that tampon pledgets are properly placed in a woman's vagina resulting in enhanced leakage protection and/or improved wearing comfort.

SUMMARY OF THE INVENTION

The present disclosure provides a tampon assembly that provides proper placement of a tampon pledget within a user's body.

The present disclosure also o provide such a tampon assembly that mitigates menses leakage.

The present disclosure provides such a tampon assembly that improves wearer comfort.

The present disclosure yet further provides such a tampon assembly having one or more insertion indicators that control the depth of insertion of the tampon pledget.

The present disclosure still further provides such a tampon assembly having one or more insertion indicators wherein the one or more insertion indicators are fixed to and/or integral with the tampon assembly.

The present disclosure also provides such a tampon assembly having one or more insertion indicators that are moveable and/or adjustable.

The present disclosure further provides such a tampon assembly having one or more fixed and/or integral insertion indicators in combination with one or more moveable and/or adjustable insertion indicators.

The present disclosure still further provides a tampon assembly wherein at least a portion of the tampon pledget housed in an applicator barrel of the assembly is visible to the user both prior to and during insertion.

The present disclosure yet further provides a tampon assembly having an adjustable plunger to gauge and/or control the insertion depth of a tampon pledget.

The present disclosure also provides a tampon assembly with a tampon pledget and removal string with one or more insertion indicators to gauge and/or control the insertion depth of the tampon pledget.

These and other advantages and benefits of the present disclosure are provided by a tampon assembly having one or more insertion indicators to gauge and/or control the insertion depth of a tampon pledget. The one or more insertion indicators may be located on the tampon applicator barrel, plunger, tampon, removal string, or any combinations thereof. As a result of the one or more insertion indicators, a woman can adjust the insertion depth of the tampon to her body's requirements ensuring leakage protection, comfort, or both.

DESCRIPTION OF THE FIGURES

FIG. 5b is an alternative embodiment of the tampon applicator of FIG. 5a;

FIG. 7a is a tampon applicator assembly having a first collapsible portion forming an insertion stop according to the present disclosure;

FIG. 7b is a tampon applicator assembly having a second collapsible portion forming an insertion stop according to the present disclosure;

FIG. 7c is a tampon applicator assembly having a third collapsible portion forming an insertion stop according to the present disclosure;

FIG. 17 is a tampon applicator assembly having a first segment connected to a second segment according to the present disclosure;

FIG. 18 is a tampon applicator assembly having a first segment disconnected from a second segment according to the present disclosure;

FIG. 19a is a tampon pledget with one or more pledget insertion indicators according to the present disclosure;

FIG. 19b is another tampon pledget with one or more pledget insertion indicators according to the present disclosure; and FIG. 20 is a segmented tampon pledget according to the present disclosure.

DETAILED DESCRIPTION OF THE INVENTION

FIGS. 4 through 20 illustrate various embodiments of the basic concept of modifying one or more tampon assembly features to ensure proper in-body placement. In many embodiments the underlying idea is the same, namely use of a "depth gauge" to gauge the depth of insertion of an applicator and/or pledget. Because women use numerous tampons, many of these design features will allow them to choose the proper "settings" to allow them to tailor a position of a tampon to the uniqueness of their own bodies. Once optimal settings have been determined by a user, they rarely need to be modified. Further, any modifications to these settings might indicate some changes taking place in a woman's body, thus alerting the user to the changes.

One such depth gauge that ensures proper in-body placement of a pledget is an applicator having a barrel with at least one insertion stop. An insertion stop may indicate to a user a distance that a barrel of a tampon applicator has been inserted into a vaginal canal, such as, for example, by feel or sensation and/or sight. As used herein, insertion stop means an insertion indicator that indicates to a user a distance that a barrel of a tampon applicator has been inserted into a vaginal canal. The position of the barrel during insertion determines a position of the pledget for proper in-body placement of the pledget. The insertion stop may indicate to a user where to position a user's fingers during insertion of the applicator. The position of the users fingers during insertion assists in placing the applicator in a proper position for proper in-body placement of a pledget.

Figure 1:
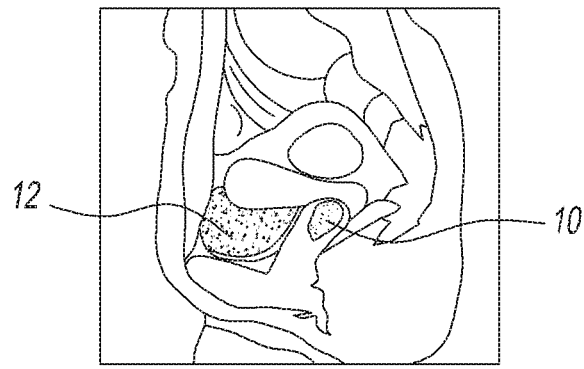
FIG. 1 is an MRI image showing a sagittal scan of a woman in her early 20's with a tampon inserted high, above the bladder.
Figure 2:
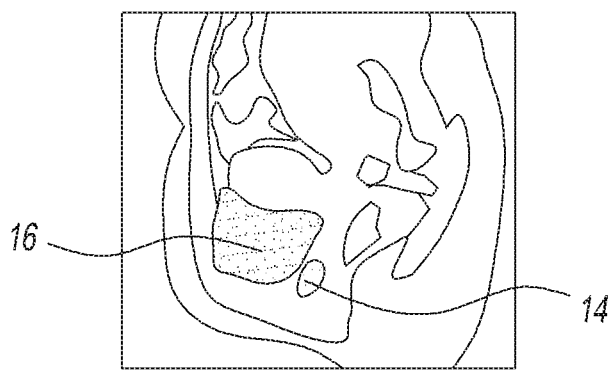
FIG. 2 is an MRI image showing a sagittal scan of another woman in her early 20's with a tampon inserted low, below the midpoint of the bladder.
Figure 3:
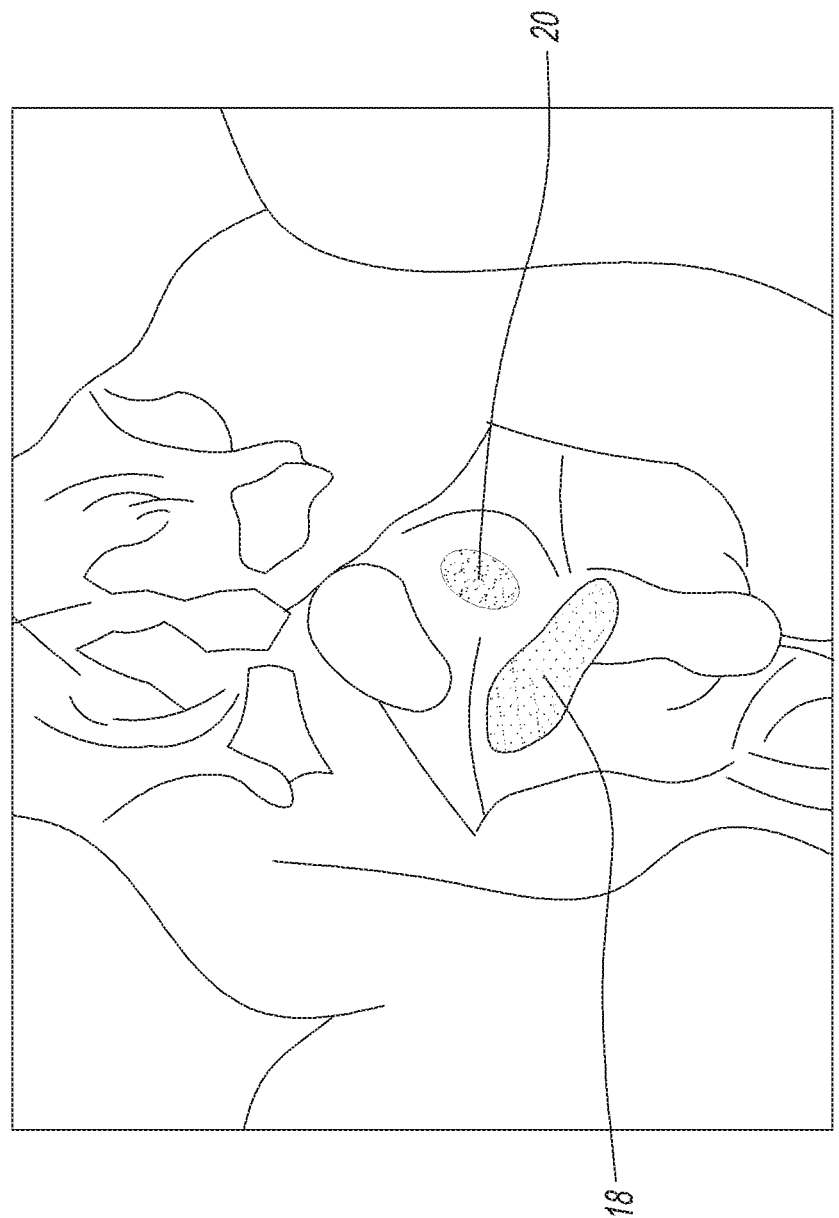
FIG. 3 is a coronal MRI scan of a 23 year old woman with a tampon inserted.
Figure 4:
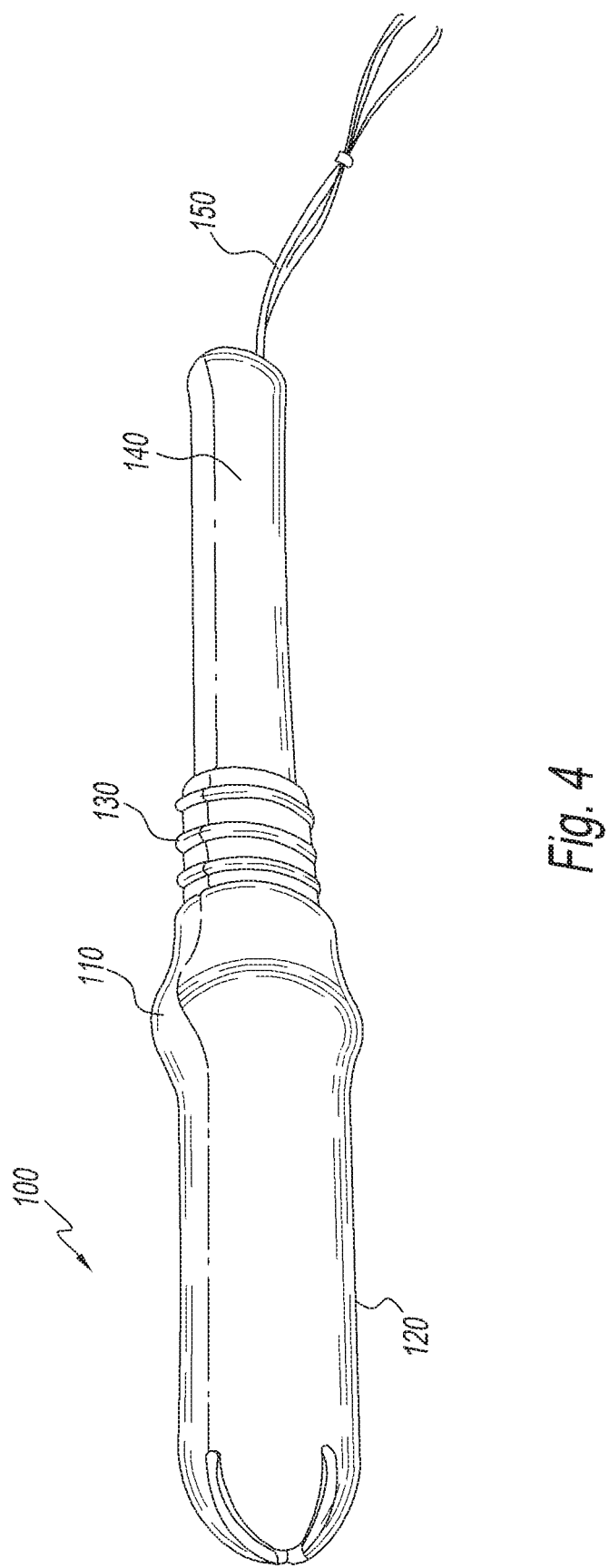
FIG. 4 is a tampon applicator assembly according to the present disclosure.

FIG. 4 shows a first exemplary embodiment of an applicator-type tampon referred to generally by reference numeral 100 with an insertion stop or indicator 110. The insertion indicator 110 is a design feature that ensures that a woman does not insert the tampon 100 too far up into her vaginal cavity: a location of the insertion indicator 110 ensures that the depth of insertion of the applicator 100 is naturally limited. A user may feel the insertion indicator 110 during insertion to indicate proper placement of the applicator 100. Applicator 100 has a barrel 120 and plunger 140. The barrel 120 is dimensioned to house a tampon pledget (not shown) therein. Preferably, the pledget is connected to a string 150 threaded through the plunger 140. The applicator 100 may further include a finger grip 130. The finger grip 130 is sized and shaped to receive one or more of the user's fingers. The barrel 120 and finger grip 130 may be a single component, as shown in FIG. 4. The insertion stop 110 may be located proximal to the finger grip 130 on the barrel 120, as shown in FIG. 4. However, the insertion stop 110 may be located anywhere along the barrel 120, finger grip 130, and/or plunger 140.

The insertion indicator 110 may have a size larger than an outer diameter of the barrel 120. The insertion indicator 110 may indicate to the user a distance that the barrel 120 has been inserted into the vaginal canal, such as, for example, by feel or sensation. The insertion indicator 110 may be a convex curve extending outward from the barrel 120, as shown in FIG. 4. While the insertion indicator 110 shown in FIG. 4 is relatively large, the insertion indicator 110 may alternatively be a simpler, smaller "rib" to limit insertion. The "rib" may be similar in shape and size to one of three ribs 130 on the finger grip 120.

The particular type, including materials, dimensions and shape, of the insertion indicator 110 that is utilized can vary according to the particular needs of tampon 100 and the environment created by the vaginal canal. The insertion indicator 110 may indicate a position of the applicator 100 without a need of fingers and shield a user's fingers from menstrual fluid during insertion. The insertion indicator 110 helps women's fingers to be kept clean and clear of menstrual fluid, which sometimes contains harmful bacteria.

Figure 5A:
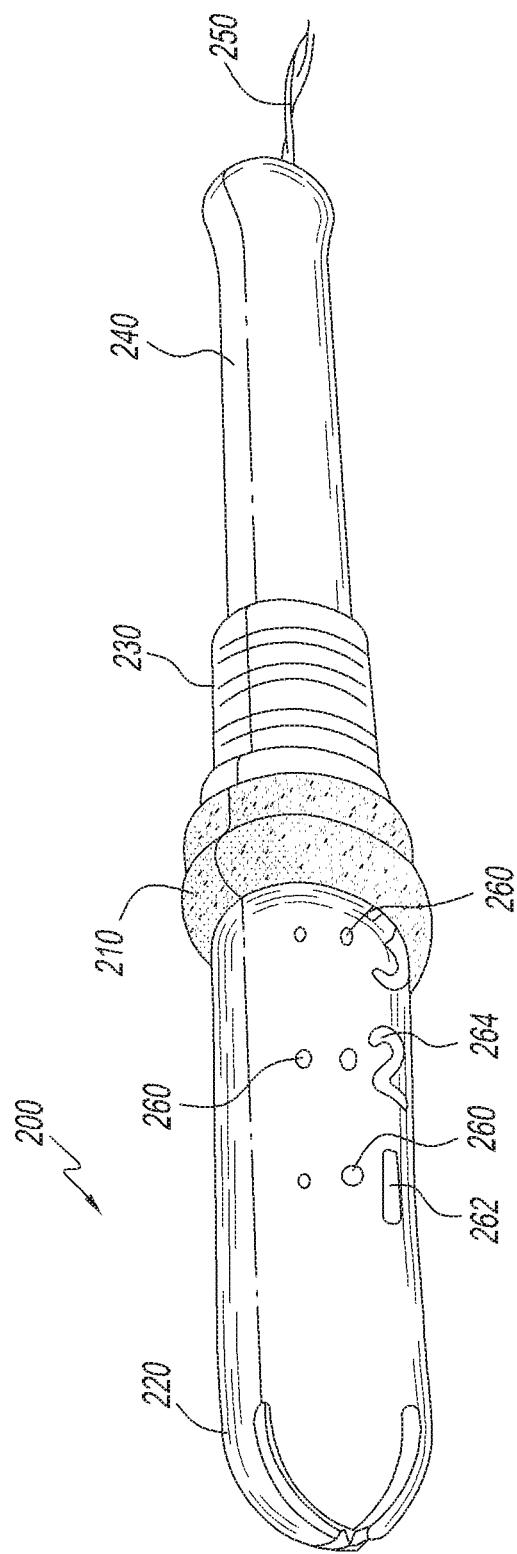
FIG. 5a is another embodiment of a tampon applicator assembly according to the present disclosure.
Figure 5B:
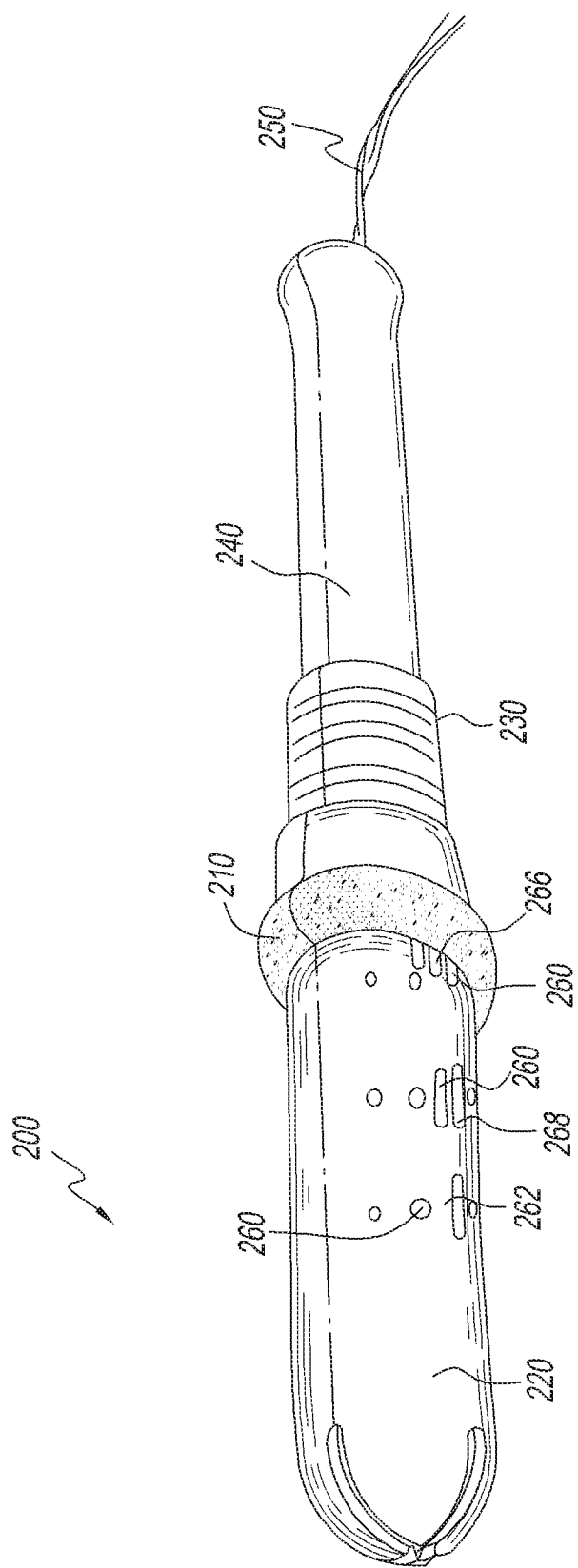

FIGS. 5a and 5b show a second embodiment of an applicator-type tampon referred to generally by reference numeral 200 with an insertion indicator 210. Similar to applicator 100 described above, applicator 200 has a barrel 220 and plunger 240. The barrel 220 is dimensioned to house a tampon pledget (not shown) therein. Preferably, the pledget has a string 250 threaded through the plunger 240. The applicator 200 may further include a finger grip 230. The finger grip 230 is sized and shaped to receive one or more of the user's fingers. The barrel 220 and finger grip 230 may be a single component, as shown in FIGS. 5a and 5b. The insertion indicator 210 may be fixed and/or integral to the barrel 220 or, preferably, is selectively moveable and/or adjustable on the barrel 220. The insertion indicator 210 may move along an outer surface of the barrel 220. The insertion indicator 210 may be a resilient material, as shown in FIG. 5a, that is, preferably, soft, comfortable medical-grade foam or a rigid material, as shown in FIG. 5b, that is, preferably, plastic.

The applicator 200 may further include calibration indices 260. The calibration indices 260, preferably, are printed on or molded directly into the applicator 200. As shown in FIGS. 5a and 5b, the calibration indices 260 may be dotted, line segments, and/or numerals. The calibration indices 260 allow a user to select a desirable positioning of the applicator 200 in the vagina and/or the insertion indicator 210 on the barrel 220 relative to the user's own unique body for optimum placement of the pledget after insertion. A user may move the insertion indicator 210 to each of the calibration indices 260.

The insertion indicator 210 may be positioned anywhere along the barrel 220. Placement of the insertion indicator 210 on or near the fingergrip 230 may sensually indicate insertion of the applicator 200 deeper than placement of the insertion indicator 210 closer to a barrel end opposite the fingergrip 230. Thus, placement of the insertion indicator 210 on or near the fingergrip 230 locates the pledget deeper into the body than placement of the insertion indicator 210 closer to the barrel end opposite the finger grip 230. In FIG. 5a, the insertion indicator 210 is positioned at a '3.5' mark. Different users may choose to position the insertion indicator 210 shallower than the '3.5' mark, such as, for example, a '1' mark 262, for a location of the pledget that reduces propensity for leakage around the pledget and/or to accommodate a shorter vaginal canal. On the other hand, the tampon applicator 200 may be inserted more deeply than the '1' mark 262, such as, for example, a setting of a '2' mark 264 for a location of the pledget that in the vaginal canal that keeps the pledget from falling out and/or to accommodate a larger vaginal canal.

In FIG. 5b, the insertion indicator 210 is positioned at a rear calibration index 266. Different users may choose to position the insertion indicator 210 shallower than the rear calibration index 266; such as, for example, an intermediate index 268 or front calibration index 262, or deeper than the rear calibration index 266 to insert the applicator 200 to reduce propensity for leakage around the tampon pledget and/or to accommodate a shorter or longer vaginal canal.

The insertion indicator 210 may indicate to the user a distance that the barrel 220 has been inserted into the vaginal canal; such as, for example; by feel; or the user may position her fingers on or near the insertion stop 210 corresponding to a pre-selected insertion depth.

Figure 6:
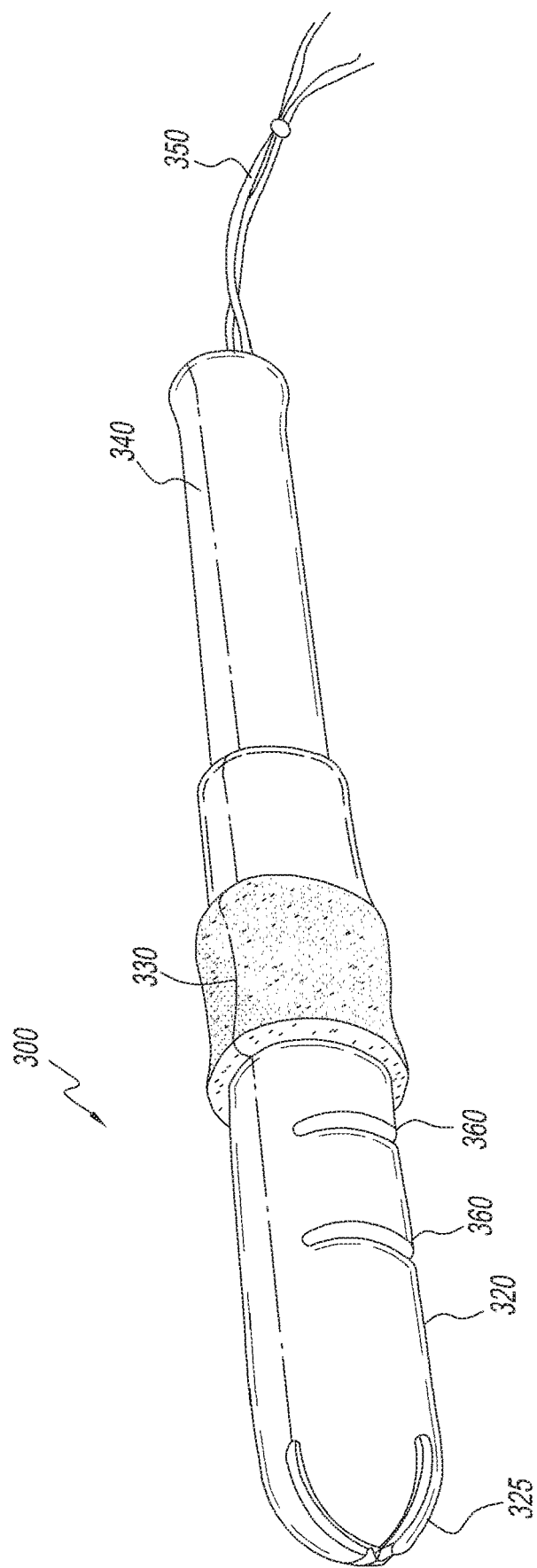
FIG. 6 is another embodiment of a tampon applicator assembly according to the present disclosure.

FIG. 6 illustrates another embodiment of an applicator-type tampon referred to generally by reference numeral 300. Similar to applicator 100 described above, applicator 300 has a barrel 320 and a plunger 340. The applicator further includes a finger grip 330. The barrel 320 is dimensioned to house a tampon pledget (not shown) therein. The tampon pledget, preferably, has a string 350 threaded through the plunger 340. The finger grip 330, preferably, is selectively movable to a plurality of finger grip positions on the barrel 320. The finger grip 330 may be a wraparound collar, as shown in FIG. 6. The finger grip 330 may be sized and shaped to receive one or more of the user's fingers. The finger grip 330, preferably, is a resilient material, and more preferably, a soft, comfortable medical-grade foam.

The user may grasp the finger grip 330 to insert the applicator 300 to a proper insertion depth into the body corresponding to one of the plurality of finger grip positions. Similar to the other embodiments, applicator 300 may be "calibrated," such as, for example, with calibration indices 360. Calibration indices indicate where to position the finger grip 330 on the barrel 320 for a proper setting or insertion depth for insertion in the body. The calibration indices 360 may be printed or molded directly on the applicator 300. The calibration indices 360 allow a user to select a desirable positioning or insertion depth of the applicator 300 and/or the finger grip 330 relative to the user's own unique body to position and insert the tampon pledget. Different users may choose to position the finger grip 330 in different positions on the barrel 320 between the plunger 340 and an insertion tip 325 on a barrel end opposite the plunger according to the user's body shape. The finger grip 330 may be moved toward the insertion tip 325 for a shallow insertion depth or in an opposite direction toward the plunger 340 for a deeper insertion depth. The finger grip 330 may be raised beyond an outer surface of the barrel 320 to sufficiently allow the finger grip 330 to function as an insertion indicator described herein. The applicator 300 may be made more aesthetically pleasing, such as, for example, by raising the finger grip portion in an elegant fashion or pattern and/or introducing color, such as, for example, a color different than a remaining portion of the applicator 300. Alternatively, the finger grip 330 may be molded and/or formed from the same material that forms the applicator 300, such as, for example, plastic and/or cardboard, in a two-part molding scheme.

Two-part molding, also known as overmolding or co-injection molding, is a process by which two plastics are molded, one on top of another, to get two different physical characteristics. For the case of tampon applicators, it is desired to have a "soft, grippy" fingergrip, but a smooth, lubricious barrel for insertion. This might be achieved first, by injection molding low density polyethylene to form the barrel, then by molding a soft, thermoplastic elastomer or a polymeric foam to form the fingergrip in a second step. This second step might be a second injection molding process, ultrasonic welding or some other comparable modification to provide a second surface.

Referring now to FIGS. 7a through 7c, another embodiment of an applicator-type tampon referred to generally by reference numeral 400 is illustrated. Similar to applicator 100 described above, applicator 400 has a barrel 420 and a plunger 440. The barrel 420 is dimensioned to house a tampon pledget (not shown) therein. Preferably, the pledget has a string 450 threaded through the plunger 440. The applicator 400 may further include a finger grip. The finger grip is sized and shaped to receive one or more of the user's fingers. The barrel 420 and finger grip may be a single component. The barrel 420 has one or more insertion indicators 410. One or more resilient or collapsible portions 460 of the barrel 420 form each of the insertion indicators 410. Segments 422 of the barrel 420 on opposite sides of each collapsible portion 460 may be moved toward one another. Two segments 422 on opposite sides of one of the collapsible portions may fold the collapsible portion outward to form one of the insertions indicators 410.

More than one of the insertion indicators 410 and collapsible portions 460 may be located at different positions along a length of the barrel 420. In FIG. 7a, the insertion indicator 410 is formed at a first collapsible portion 462 closest to the insertion tip 425 of the applicator 400. In FIG. 7c, the insertion indicator 410 is formed at a third collapsible portion 466 closest to the plunger 440. In FIG. 7b, the insertion indicator 410 is formed at a second collapsible portion 464 intermediate the first collapsible portion 462 and the third collapsible portion 466.

The user may select a desired position of an insertion indicator from the different positions. A collapsible portion corresponding to the desired position may be folded outward to form the desired indicator or stop. Additional insertion stops may also be formed. Any insertion stops that are not selected by the user may remain unfolded during insertion. An insertion indicator 410 on or near an insertion tip 425 indicates a shallower insertion depth of the pledget and/or applicator 400. An insertion indicator 410 on the barrel 420 that is closer to the plunger 440 than the insertion tip 425 indicates a deeper insertion depth of the pledget and/or applicator 400.

Figure 8:
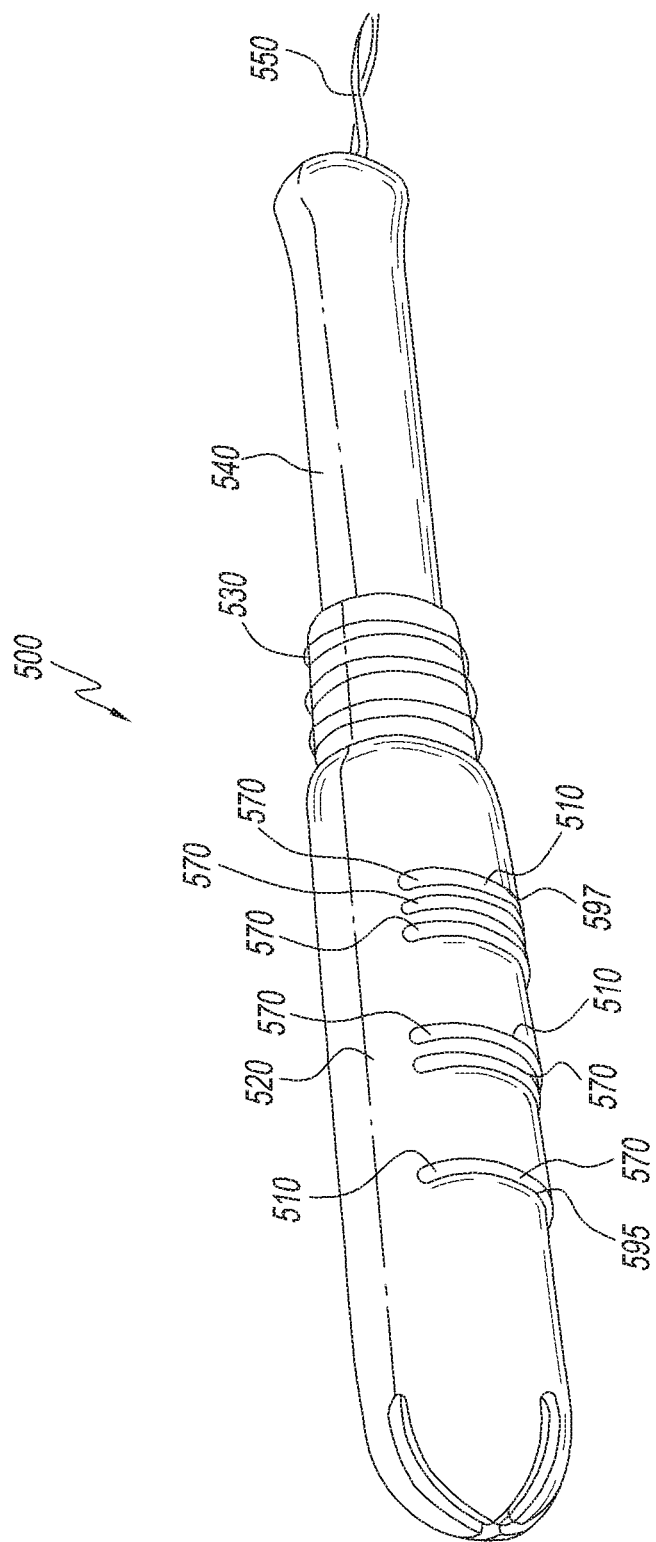
FIG. 8 is another tampon applicator assembly according to the present disclosure.

FIG. 8 illustrates another embodiment of an applicator-type tampon referred to generally by reference numeral 500 with one or more insertion indicators 510. Similar to applicator 100 described above, applicator 500 has a barrel 520 and plunger 540. The barrel 520 is dimensioned to house a tampon pledget (not shown) therein. Preferably, the pledget has a string 550 threaded through the plunger 540. The applicator 500 may further include a finger grip 530. The finger grip 530 is sized and shaped to receive one or more of the user's fingers. The barrel 520 and finger grip 530 may be a single component, as shown in FIG. 8.

The insertion indicators 510 may be one or more ribs 570 extending outward from the barrel 520. The one or more ribs 570 may be molded-in index graphics. The molded-in index graphics may include, for example, line segments extending from an outer surface of the barrel 520.

The one or more ribs 570 are positioned along a length of the barrel 520 to indicate deeper and shallower positions of the applicator 500 in the body. The one or more ribs 570 may indicate to the user a distance of the barrel 520 that is inserted into the vaginal canal, for example, by feel or sight. The user may position her fingers on one or more of the ribs 570 to visually indicate a distance that the barrel 520 is to be inserted into the vaginal canal. The user may position her fingers on a front-most ring 595 to ensure a low depth of insertion of the applicator 500, or on a rearmost ring 597 to ensure a much deeper insertion level, if desired. The pledget is located deeper in the vaginal canal when the applicator 500 has a deeper insertion level than the low depth of insertion. The front-most ring 595, the rear-most ring 597, and intermediate rings between the front-most ring 595 and the rear-most ring 597 allow a user to position the applicator 500 relative to the user's own unique body to position.

Alternatively, the one or more ribs 570 may be seven different raised finger grip "ribs" or rings positioned equidistantly from one another. The user may position her fingers on a front-most ring to ensure a low depth of insertion, or on the rearmost ring to ensure a much deeper insertion level, if desired.

Figure 9:
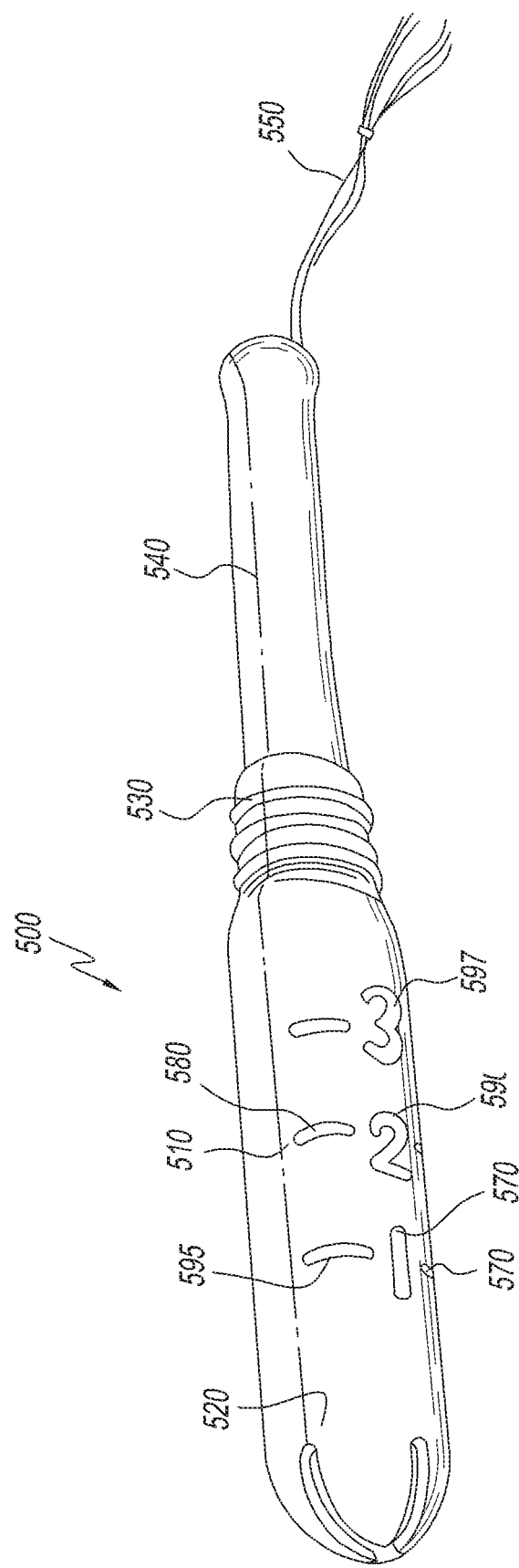
FIG. 9 is an alternative embodiment of the tampon applicator assembly according to the present disclosure.

Another alternative of applicator 500 is illustrated in FIG. 9. The one or more ribs 570 are flush or printed on the applicator 500. The one or more ribs 570 may be a line segment 580 and a numeral 590. Here the design feature is a calibrated applicator barrel. The user inserting the tampon simply inserts the applicator 500 to the desired calibrated setting or line segment 580 and numeral 590 to accommodate their anatomical needs. Most women do not or cannot view the applicator while inserting the tampon. The user may use the one or more ribs 570, for example, to position one or more fingers on the applicator 500.

Another depth gauge that ensures proper in-body placement of a pledget is an applicator having finger indicators. The finger indicators indicate to a user where to position a user's fingers during insertion of the applicator. The position of the user's fingers during insertion assists in placing the applicator in a proper position for proper in-body placement of a pledget.

Figure 10:
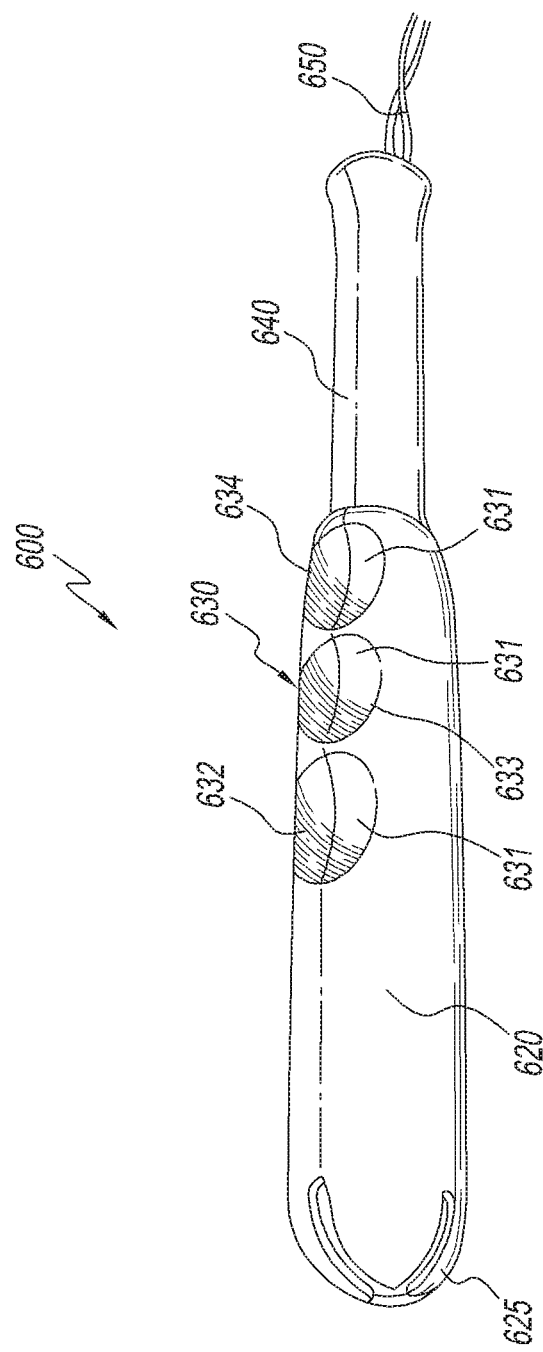
FIG. 10 is a tampon applicator assembly having finger indicators according to the present disclosure.
Figure 11:
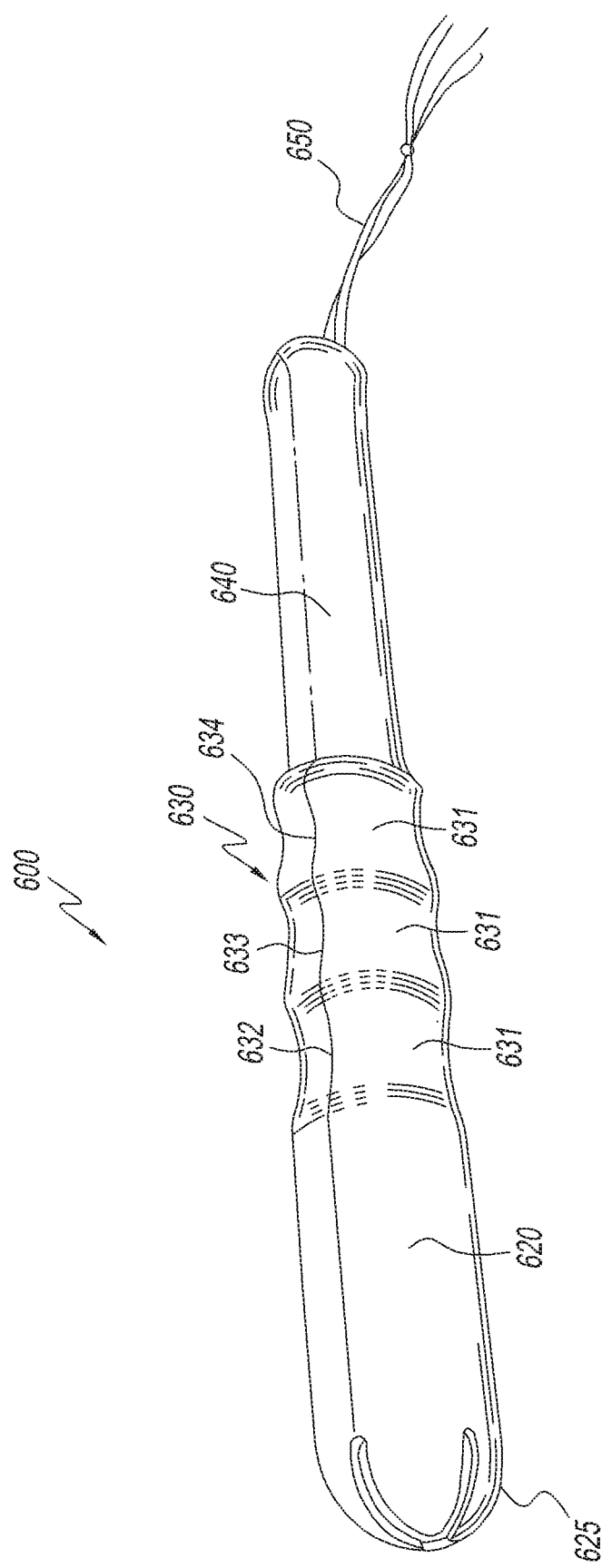
FIG. 11 is an alternative embodiment of the tampon applicator assembly of FIG. 10.

FIGS. 10 and 11 depict additional embodiments of an applicator-type tampon according to the present invention referred to generally by reference numeral 600 with a finger grip 630. Similar to applicator 100 described above, applicator 600 has a barrel 620 and plunger 640. The barrel 620 is dimensioned to house a tampon pledget (not shown) therein. Preferably, the pledget has a string 650 that is threaded through the plunger 640. The barrel 620 and finger grip 630 may be an integrally formed as a single component, as shown in FIGS. 10 and 11, or the barrel 620 and finger grip 630 may be formed separately and subsequently attached (not shown). The finger grip 630 is sized and shaped to receive one or more of the user's fingers. The finger grip 630 has one or more finger indicators 631 at different locations along an outer surface of the barrel 620. The finger indicators may be, for example, molded-in finger indicators, as shown in FIGS. 10 and 11. The finger indicators 631 may be concave depressions, as shown in FIG. 10, or finger grip 630 may be scalloped to provide finger indicators 631, as shown in FIG. 11. The user may select a desirable positioning of the applicator 600 relative to the user's own unique body by grasping the one or more finger indicators 631 at the different locations along the applicator 600. Different users may choose to grasp first finger indicators 632 closest to an insertion tip 625 of the barrel, second finger indicators 633, and/or third finger indicators 634 closest to plunger 640 to position applicator 600 and the tampon pledget deeper or shallower into the vaginal canal. The user may grasp the first finger indicators 632 to assist in positioning the applicator 600 and pledget shallower in the vaginal canal than the user grasping the second or third finger indicators 633 and 634. The user may grasp the second finger indicators 633 to assist in positioning the applicator 600 and pledget shallower in the vaginal canal than the user grasping the third finger indicators 634 and deeper than the user grasping the first finger indicators 632. The user may grasp the third finger indicators 634 to assist in positioning the applicator 600 and pledget deeper in the vaginal canal than the user grasping the first or second finger indicators 632 and 633.

Another depth gauge that ensures proper in-body placement of a pledget is an applicator that has the pledget visible therethrough. For example, the pledget may be visible through the barrel of the applicator. One advantage of the pledget being visible through the applicator is that the user may see a position of the pledget in the barrel, e.g., closer to a plunger or an insertion tip of the applicator, allowing a user to gauge a distance to depress the plunger for proper in-body placement of the pledget.

Figure 12:
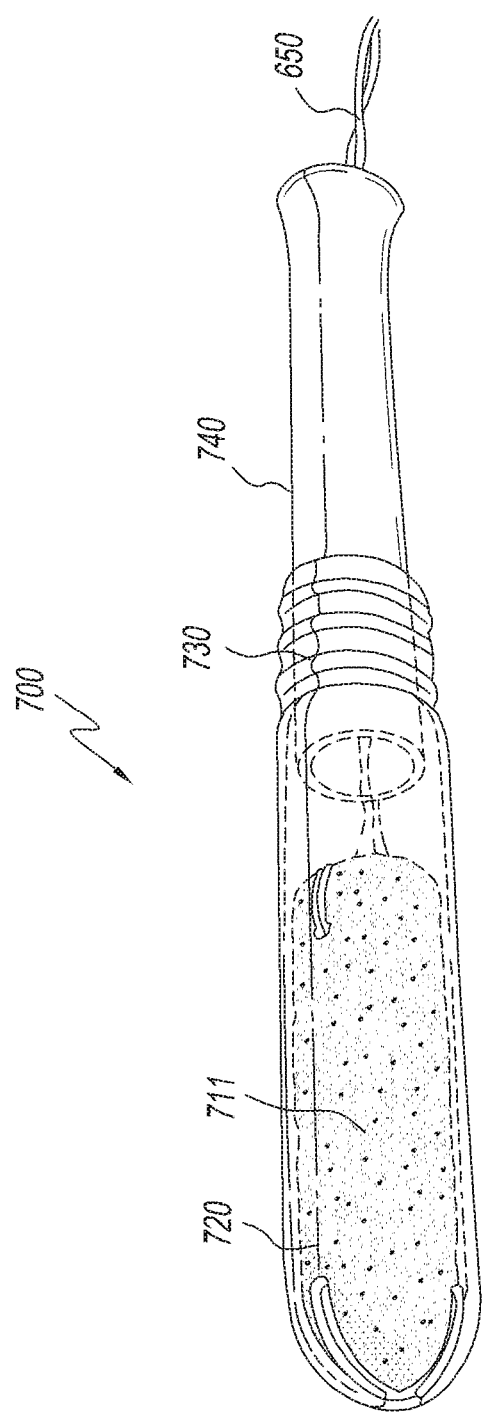
FIG. 12 is another embodiment of a tampon applicator assembly according to the present disclosure.
Figure 13:
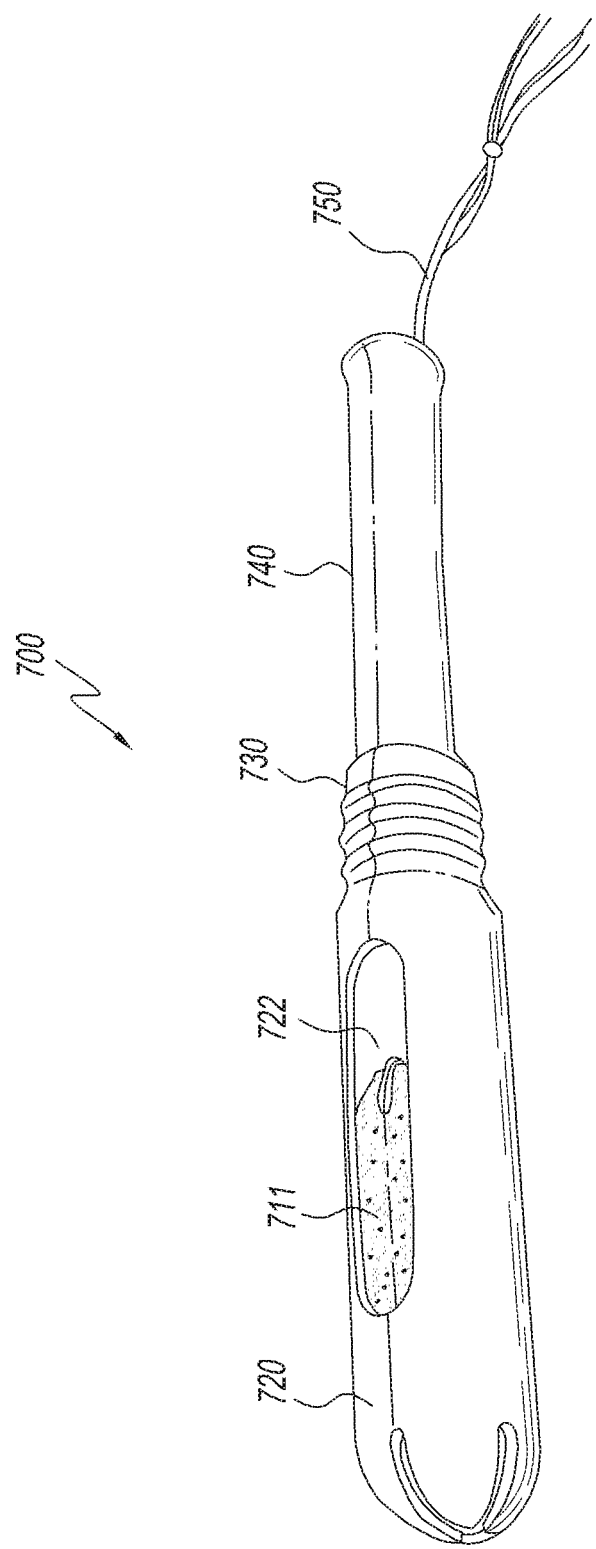
FIG. 13 is an alternative embodiment of the tampon applicator assembly of FIG. 12.
Figure 14:
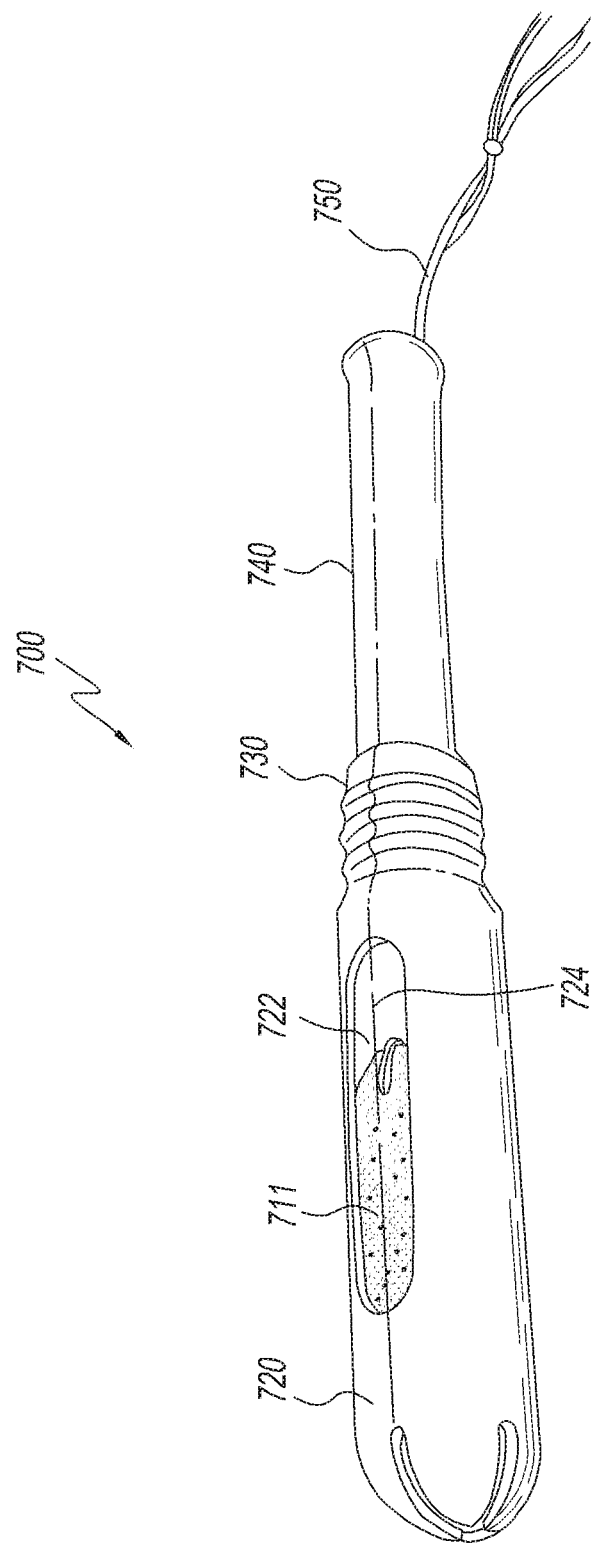
FIG. 14 is another alternative embodiment of the tampon applicator assembly of FIG. 12.

FIGS. 12 through 14 illustrate another embodiment of an applicator-type tampon applicator assembly according to the present invention referred to generally by reference numeral 700. The applicator 700 has a barrel 720 and plunger 740. The barrel 720 is dimensioned to house a pledget 711 therein. Preferably, the pledget 711 has a string 750 that is threaded through the plunger 740. The applicator 700 may further include a finger grip 730. The finger grip 730 is sized and shaped to receive one or more of the user's fingers. The barrel 720 and finger grip 730 may be a single component, as shown in FIGS. 12 through 14. The barrel 720 has an interior that is visible through at least a portion of said barrel. The pledget 711 is visible through the applicator barrel 720. The user may insert the pledget 711 more easily when the pledget 711 is visible through applicator 700. As shown in FIG. 12, the barrel 720 may be clear or transparent to form a clear housing. As shown in FIG. 13, the barrel 720 may have an opening 722 through applicator 700 exposing the pledget 711. The opening 722 may be covered by a clear or transparent layer 724 to form a window in the applicator 700, as shown in FIG. 14.

Another depth gauge that ensures proper in-body placement of a pledget is a plunger that has one or more plunger stops. One advantage of the one or more plunger stops allows a user to gauge a distance of the plunger depressed for proper in-body placement of the pledget. The plunger has a length that may be adjusted. Adjusting the length increases or decreases a distance the pledget may be inserted into the body for proper in-body placement of the pledget.

Figure 15:
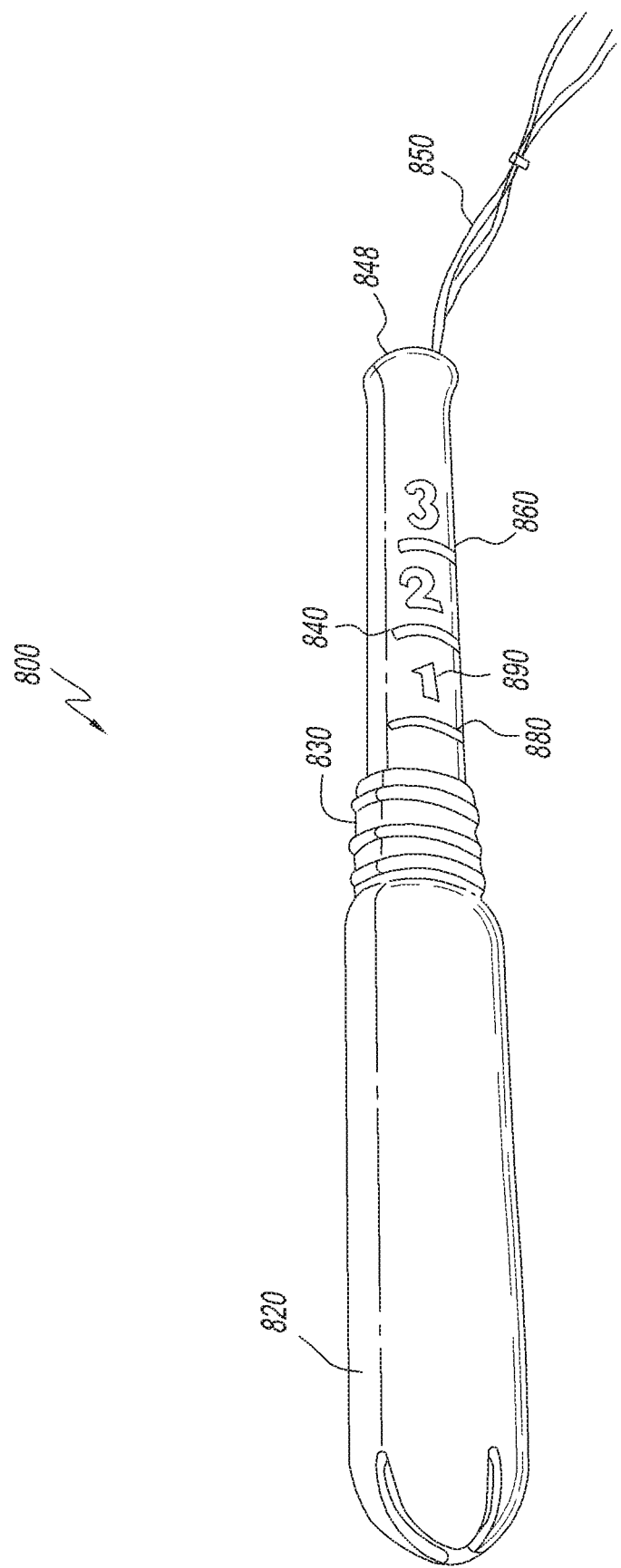
FIG. 15 is another embodiment of a tampon applicator assembly according to the present disclosure.

FIG. 15 illustrates yet another embodiment of an applicator-type tampon assembly according to the present invention referred to generally by reference numeral 800. Similar to applicator 100 described above, applicator 800 has a barrel 820 and plunger 840. The barrel 820 is dimensioned to house a tampon pledget (not shown) therein. Preferably, the pledget has a string 850 threaded through the plunger 840. The applicator 800 may further include a finger grip 830. The finger grip 830 is sized and shaped to receive one or more of the user's fingers. The barrel 820 and finger grip 830 may be a single component, as shown in FIG. 15. Similar to the barrels described above, the plunger 840 may be calibrated. For example, plunger markings or "stops" 860 may be placed on the plunger 840, in much the same way that these markings or stops appear on the applicator barrel, as previously described. The plunger 840 may have one or more plunger stops 860 between a first plunger end (not shown) that is inserted into the barrel 820 and a second plunger end 848 that is opposite to the first plunger end. The plunger stops 860 at or near the first plunger end provide shallower insertion depths of the pledget than plunger stops at or near the second plunger end 848. Preferably, the stops 860 are one or more molded-in index graphics, and more preferably, the stops include one or more molded-in index graphics of a plunger line segment 880 and/or a plunger numeral 890. The plunger 840 may be used with any of the embodiments described herein.

Effective deployment of the above design features sometimes suggests changes in women's habits and practices in inserting a tampon. For example, to use the calibrated plunger depicted in FIG. 15 most effectively, the tampon applicator 800 would be inserted normally into a vagina, and then the tampon pledget is ejected by depressing the plunger 840 up to a pre-selected plunger stop 860. The user may visually or sensually gauge how far the plunger 840 is depressed into the barrel 820. The barrel 820 is then retracted until the barrel 820 exits the vagina, leaving the tampon pledget in a desired position in the vaginal canal to assure leakage protection and comfort.

Figure 16A:
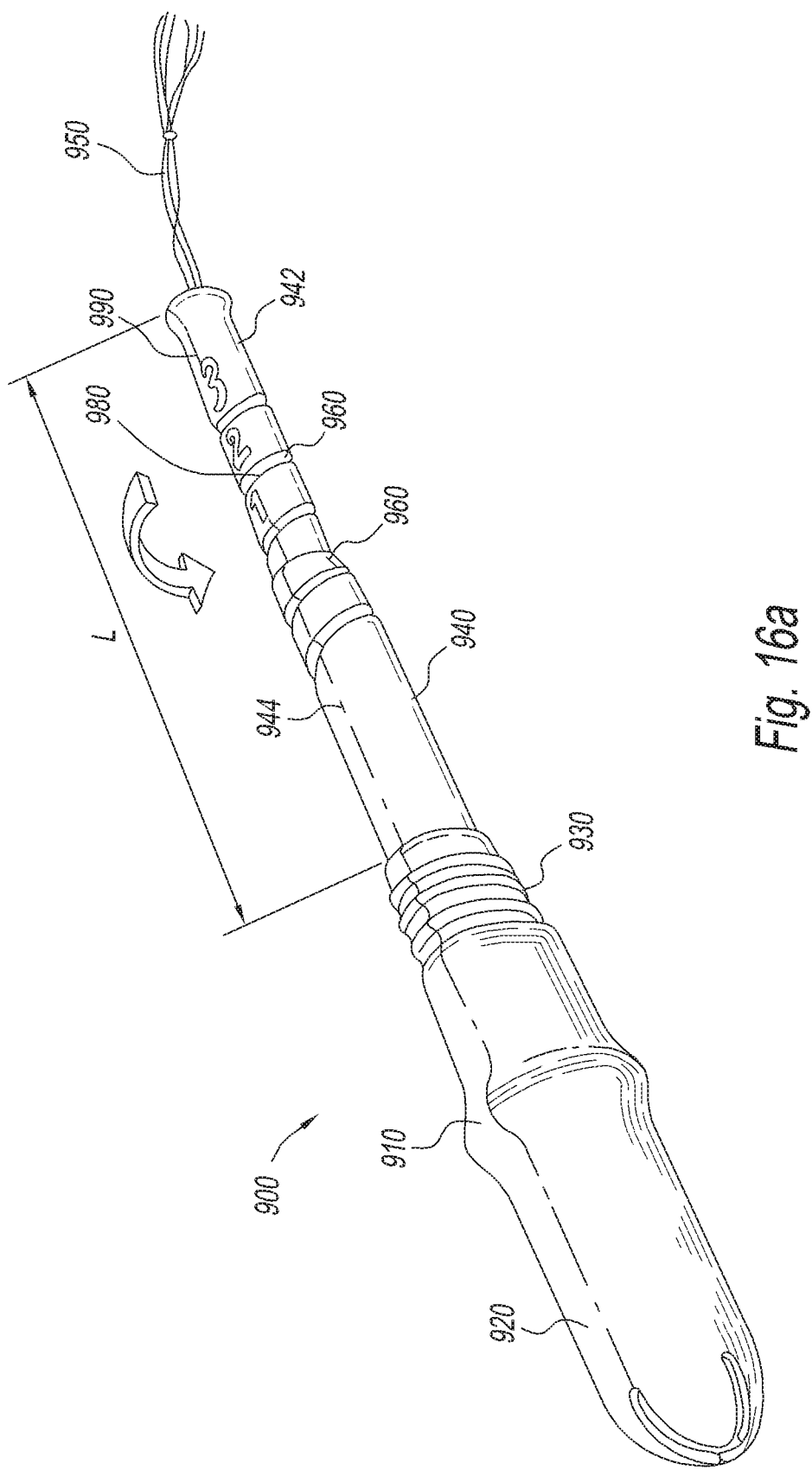
FIG. 16a is a tampon applicator assembly having an inner plunger in a first position according to the present disclosure.
Figure 16B:
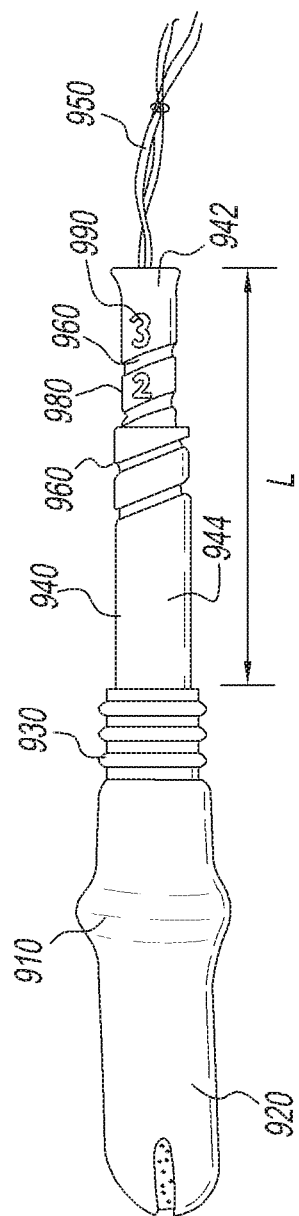
FIG. 16b is a tampon applicator assembly having an inner plunger in a second position according to the present disclosure.
Figure 16C:
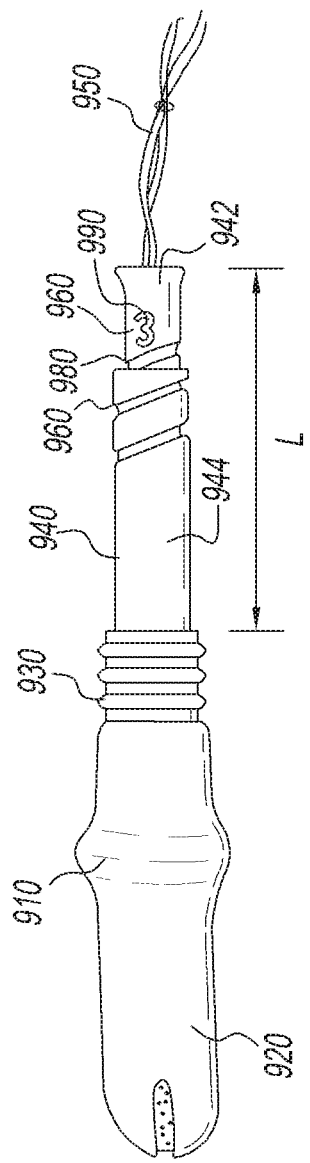
FIG. 16c is a tampon applicator assembly having an inner plunger in a third position according to the present disclosure.

Referring now to FIGS. 16a through 16c, another embodiment of an applicator-type tampon assembly according to the present invention referred to generally by reference numeral 900 is illustrated. Similar to applicator 100 described above, applicator 900 has a barrel 920. The barrel 920 is dimensioned to house a tampon pledget (not shown) therein. Preferably, the pledget has a string 950 threaded through a plunger 940. The applicator 900 may further include a finger grip 930 and/or an insertion indicator 910. The insertion indicator 910 may be any type insertion stop, such as, for example, an insertion indicator described herein. The finger grip 930 is sized and shaped to receive one or more of the user's fingers. The barrel 920 and finger grip 930 may be a single component, as shown in FIGS. 16a through 16c. The applicator 900 has two, interlocking plungers 942 and 944. An inner plunger 942 is inside another, outer plunger 944. Preferably, the inner and outer plungers 942 and 944 are two slightly different lengths, such that the outer plunger 944 would make ejection easy with the outer and inner plungers 942 and 944 placing the applicator 900 in a proper position in the body. The inner plunger 942 may increase a total length L of the plunger 940. The inner plunger 942 extends out of the outer plunger 944 to increase or decrease the total length L and as a result vary the insertion depth of the pledget into the body.

Similar to the barrels described above, the plunger 940 may be calibrated. For example, markings, indicators or "stops" 960 may be placed on the plunger 940, in much the same way that these markings or indicators appear on the applicator barrel. The indicators 960 may be on the inner plunger 942, the outer plunger 944, or any combination thereof. Preferably, the indicators 960 are one or more molded-in index graphics, and more preferably, the indicators include one or more molded-in index graphics of a plunger line segment 980 and a plunger numeral 990.

The inner plunger 942 may be in a plurality of different positions within the outer plunger 944. For example, the inner plunger 942 may have a first position indicated by one of the indicators 960, as shown in FIG. 16a, to provide placement of the pledget deeper or higher up into the vaginal canal after insertion into the vagina. The inner plunger 942 may have a second position indicated by one of the indicators 960, as shown in FIG. 16b, in which the inner plunger 942 is closer to the finger grip 930 than the first position. The second position places the pledget lower or shallower in the vaginal cavity than the first position. The inner plunger 942 may be in a third position indicated by one of the indicators 960, as shown in FIG. 16c, in which the inner plunger 942 is closer to the fingergrip 930 than the first position and the second position. The third position places the pledget lower or shallower in the vaginal cavity than the first or second positions. The inner plunger 942 may be positioned anywhere along its length inside of the outer plunger 944, but the inner plunger should not extend distally past the most distal part of the outer plunger. The use of the indicator on the barrel together with the calibration indices 960 on the plunger 940 allows the tampon pledget to eject to the desirable place inside the vagina, without the need to retract the barrel 920 to a specified point. An additional advantage would be that a two-plunger design tends to eject the tampon pledget so that less force is required owing to additional force available from a second plunger. The two plungers together would be "stiffer", since the overall thickness of both would exceed that of each individually. Additionally, the "two-step" operation would reduce the total force required for a single-step operation.

Referring now to FIGS. 17 and 18, a further embodiment of an applicator-type tampon assembly according to the present invention is illustrated generally by reference numeral 1000. Applicator 1000 has a plunger 1040 with one or more segments 1042. A first segment 1044 may be connected to a second segment 1046, as shown in FIG. 17. The first segment 1044 may be detached from the second segment 1046 to decrease the length L, as shown in FIG. 18. One or more segments 1042 increase or decrease a length L of plunger 1040. For example, to use the plunger 1042 depicted in FIGS. 17 and 18 most effectively, an applicator 1000 would be inserted normally into a vagina; and then a pledget (not shown) would be ejected by pushing the length of the plunger 1040 into the barrel 1020. The barrel 1020 is then retracted until the barrel 1020 exits the vagina, leaving the pledget in a desired position in the vaginal canal to assure leakage protection and comfort. Increasing the length L of the plunger 1040 positions the pledget deeper into the vagina. Decreasing the length L of the plunger 1040 positions the pledget shallower into the vagina. Although two of the one or more segments 1042 are illustrated in FIGS. 17 and 18, any number of segments 1042 may be used to form the novel plunger of the present invention. Plunger 1040 may be used with any of the embodiments included herein.

Referring to FIGS. 19a and 19b, a tampon pledget 1100 may have one or more pledget insertion indicators 1110, according to another embodiment of the present invention. The pledget insertion indicators 1110 are design features similar to insertion indicators described herein that could be applied to a string 1150 of the pledget 1100 to achieve a similar purpose of regulating the level of insertion. The user may insert the pledget 1100 into the vagina as she does normally, then pull back gently on the string to an appropriate stop of the one or more pledget insertion indicators 1110. The appropriate indicator indicates a position of the pledget 1100 or a proper level of insertion for the user's own unique body, for example, by feel or sight. The particular type, including materials, dimensions and shape, of the one or more pledget insertion indicators 1110 that is utilized can vary according to the particular needs of pledget 1100 and the environment created by an applicator or the vaginal canal. For example, the one or more pledget insertion indicators 1110 may be knots, as shown in FIG. 19a, or foam beads, as shown in FIG. 19b.

A pledget may be designed to accommodate women's anatomical variations and needs during menstruation. One simple change may be to "segment" the pledget. Referring to FIG. 20, a segmented pledget 1200 is depicted. Segmented pledget 1200 has two or more segments 1210. The pledget may be segmented by using pressure or anisotropic crimping or by stringing together multiple fibrous pads or webs. The top part of the pledget may catch or absorb fluid as directed from the cervical os, whereas a bottom portion of the pledget may catch or absorb fluid that would be likely to bypass the pledget. The pledget may have a slight curvature. The pledget may be more flexible in certain segments to conform to a curvature typical of the vaginal canal. Alternatively, the segments 1210 of the pledget may be separated by judiciously placed knots (not shown) on a string 1230 to cover the vaginal canal most effectively. Longer vaginal canals would be accommodated by knots that would widely space pledget segments 1210. Shorter canals might require virtually no spacing or a single pledget segment. In such a manner, the proper pledget segments can be properly placed inside the vagina to achieve both leakage protection and comfort.

Yet another embodiment of this invention may use chemical rather than physical means to ensure proper tampon placement. That is, a very smooth, lubricious first coating could be applied to an applicator barrel tip. A second coating that is a much coarser, more abrasive finish (or even "flocking") than the first coating may be applied to another end of the tampon applicator opposite the applicator barrel tip. The front-most portion would gently allow the applicator to slide into the woman's vaginal canal easily and comfortably, but the rearmost, more "abrasive" portion would sort of naturally limit insertion: a slight change in "feel" would alert the woman that she has inserted the tampon to a pre-selected point.

The applicators of the present invention may have any combination of the features of the embodiments described herein. The particular type, including materials, dimensions and shape, of the applicator and/or pledget that is utilized can vary according to the particular needs of the tampon and the environment created by the vaginal canal. For example, the applicator may be a material including, for example, biopolymer, biopolymers including polysaccharides and proteins, cardboard, heat shrink plastic, paper, paper or cardboard laminate, paper slurry, plastic, plastic tubing, pulp slurry, pulp-molded paper, mechanical pulp, chemical pulp including sulfite, bisulfite, and sulfate types, thermo-mechanical pulp, chemi-thermo-mechanical pulp, recycle pulp including pre- and post-consumer types, synthetic pulp including polyethylene and polypropylene types, or any combinations thereof. The applicator may be manufactured by spiral wound cardboard, convolutely wound cardboard, injection molding, molding from pulp based materials, and any combinations thereof.

The above embodiments are by no means exhaustive. To one skilled in the art, to be sure, there are other, related design features and concepts that focus on improved tampon placement. These, too, should be covered in the invention. While the instant disclosure has been described with reference to one or more exemplary embodiments, it will be understood by those skilled in the art that various changes may be made and equivalents may be substituted for elements thereof without departing from the scope thereof. In addition, many modifications may be made to adapt a particular situation or material to the teachings of the disclosure without departing from the scope thereof. Therefore, it is intended that the disclosure not be limited to the particular embodiment(s) disclosed as the best mode contemplated for carrying out this invention.

We claim:

1. A tampon applicator assembly, comprising:
   a tampon pledget having a longitudinal axis such that a top part and a bottom part adjacent and connected to said top part are positioned along said longitudinal axis, said top part and said bottom part having different levels of flexibility, said tampon pledget further comprising a removal string attached to said bottom part; and
   a tampon applicator, comprising:
      a barrel region that is lubricious and comprises low density polyethylene having an insertion tip and a second end, said barrel region having dimensions to house said tampon pledget therein;

a grip region having a barrel end adjacent said second end of said barrel region, said grip region having a plunger receiving end opposite said barrel end, said grip region sized and shaped to receive one or more of a user's fingers, said barrel and said grip region are a single component, said grip region comprising one or more markings; and a plunger having a forward end and a rearward end;

wherein said string is threaded through said plunger;

wherein said plunger forward end pushes said pledget through the barrel and out said insertion tip to a selected insertion depth;

wherein said top part comprises a first segment that catches and/or absorbs fluid;

wherein said bottom part comprises a second segment catches and/or absorbs fluid that would be likely to bypass said top part; and wherein said-top part and said bottom part having different levels of flexibility enables said pledget to conform to a curvature along said longitudinal axis where said bottom part is at an angle with respect to said top part.

2. The tampon applicator assembly of claim 1, wherein said grip region comprises one or more ribs.

3. The tampon applicator assembly of claim 2, wherein said one or more ribs comprise a first gripping rib and a second gripping rib such that said first gripping rib is closer to said insertion tip than said second gripping rib, wherein said user may grip said tampon applicator about said first gripping rib to ensure a low depth of insertion, wherein said user may grip said tampon applicator about said second gripping rib to ensure a deeper insertion.

4. The tampon applicator assembly of claim 2, wherein said one or more ribs on said grip region comprises a front-most ring and a rear-most ring, and one or more intermediate rings, wherein said user may position said user's one or more fingers on said front-most ring to provide a shallower insertion depth, wherein said user may place said user's one or more fingers on said rear-most ring to provide a deeper insertion depth.

5. The tampon applicator assembly of claim 1, wherein said tampon applicator further comprises an insertion indicator.

6. The tampon applicator assembly of claim 5, wherein said insertion, indicator comprises a convex curve.

7. The tampon applicator assembly of claim 6, wherein said convex curve forms one or more ribs extending outward from said applicator.

* * * * *